(12) United States Patent
Tanner et al.

(10) Patent No.: US 6,371,919 B1
(45) Date of Patent: Apr. 16, 2002

(54) METHOD AND APPARATUS FOR THE SURGICAL REPAIR OF ANEURYSMS

(75) Inventors: Howard Tanner, Logan, UT (US); Hugh Trout, III, Washington, DC (US); Ronald Ehmsen, Villa Park, CA (US)

(73) Assignee: EVA Corporation, Bethesda, MD (US)

( * ) Notice: Subject to any disclaimer, the term of this patent is extended or adjusted under 35 U.S.C. 154(b) by 0 days.

(21) Appl. No.: 09/108,190

(22) Filed: Jul. 1, 1998

Related U.S. Application Data

(62) Division of application No. 08/896,415, filed on Jul. 18, 1997.
(60) Provisional application No. 60/051,209, filed on Jun. 30, 1997.

(51) Int. Cl.7 .................................................. A61B 8/14
(52) U.S. Cl. ....................................... 600/462; 600/463
(58) Field of Search ................................ 600/437, 461, 600/462, 463, 464, 467, 476, 478, 549, 585, 474, 407; 604/118, 504, 96.01, 264, 101; 606/9, 10, 11, 12

(56) References Cited

U.S. PATENT DOCUMENTS

| | | | | |
|---|---|---|---|---|
| 4,445,892 A | * | 5/1984 | Hussein et al. ............. | 604/101 |
| 4,562,596 A | | 1/1986 | Kornberg | |
| 4,787,899 A | | 11/1988 | Lazarus | |
| 4,848,336 A | * | 7/1989 | Fox et al. ................. | 128/303.1 |
| 5,042,707 A | | 8/1991 | Taheri | |
| 5,427,107 A | * | 6/1995 | Milo et al. .................... | 600/463 |
| 5,456,258 A | * | 10/1995 | Kondo et al. ................ | 600/462 |
| 5,671,748 A | * | 9/1997 | Itoi ............................. | 600/462 |
| 5,676,696 A | * | 10/1997 | Marcade ......................... | 623/1 |
| 5,690,117 A | * | 11/1997 | Gilbert ........................ | 600/462 |
| 5,871,449 A | * | 2/1999 | Brown ......................... | 600/474 |
| 5,935,075 A | * | 8/1999 | Casscells et al. ............ | 600/474 |
| 5,957,849 A | * | 9/1999 | Munro ......................... | 600/462 |
| 5,957,899 A | * | 9/1999 | Spears et al. ................ | 604/264 |
| 6,245,026 B1 | * | 6/2001 | Campbell et al. ............ | 600/549 |

* cited by examiner

Primary Examiner—Marvin M. Lateef
Assistant Examiner—Ali M. Imam
(74) Attorney, Agent, or Firm—John N. Coulby; Collier Shannon Scott PLLC

(57) ABSTRACT

An attachment assembly and repair graft are disclosed for securing a graft to repair a vessel having an aneurysm therein. The attachment assembly comprises an attachment cuff such that the graft is not dimensionally dependent upon the size of the vessel. A visualization apparatus is also disclosed for real time direct viewing of an interior of a vessel. A penetration apparatus is disclosed for use in forming treatment specific holes in a potentially calcified vessel wall which facilitates thereafter the securing of the graft and attachment assembly to the vessel wall. An introducer sheath device is also disclosed that comprises a sealing assembly for preventing the loss of blood from the vessel during the insertion and subsequent removal of surgical components during the surgical procedure.

55 Claims, 26 Drawing Sheets

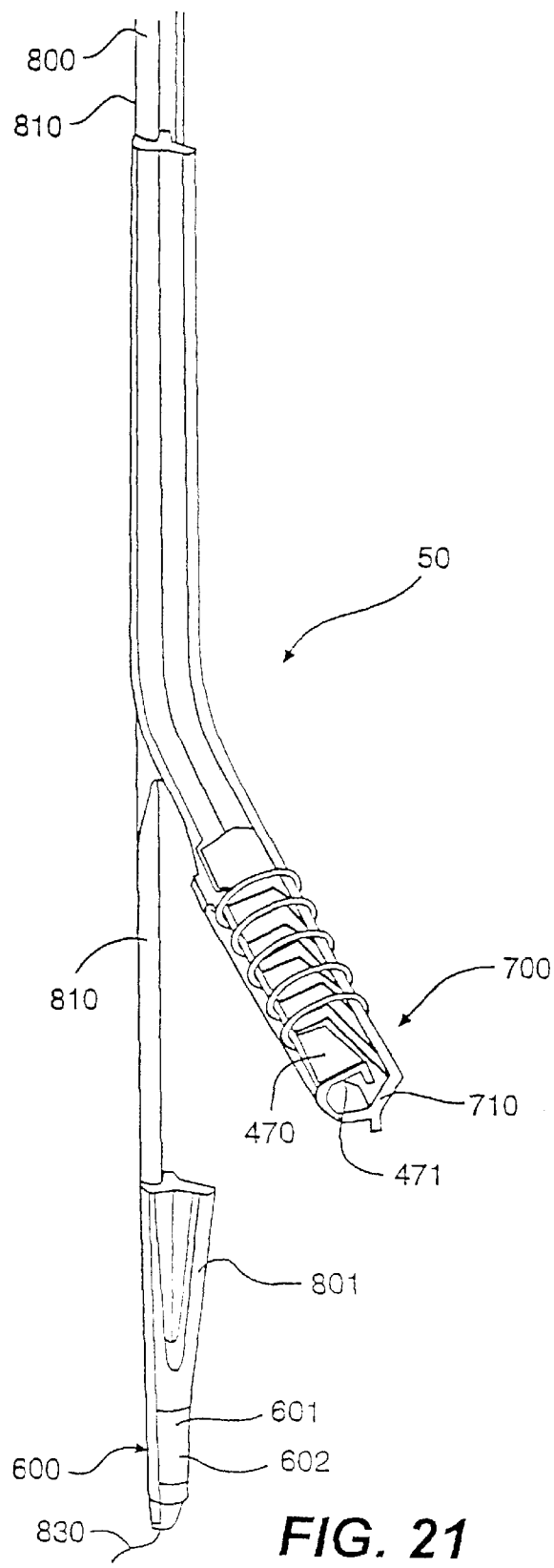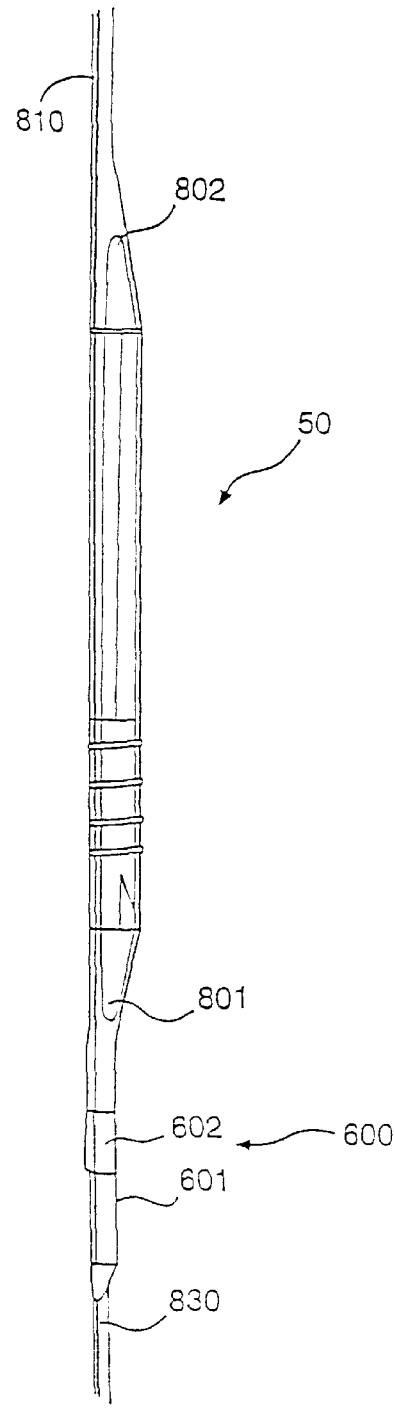
FIG. 21
FIG. 22

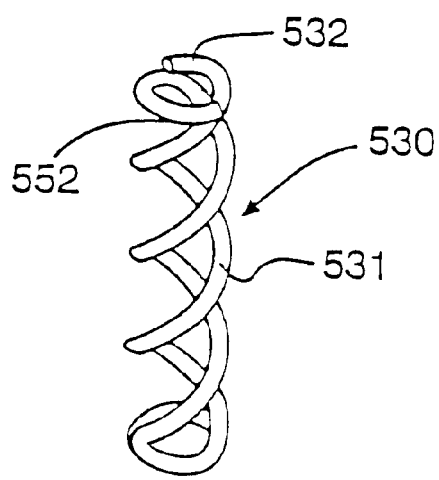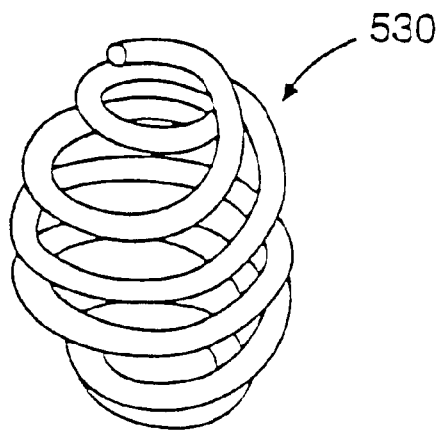
FIG. 29
FIG. 30
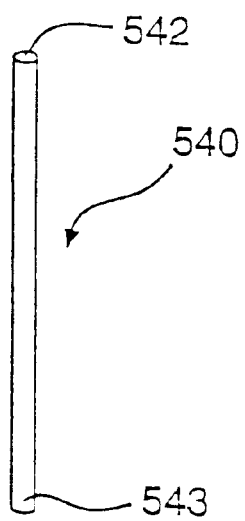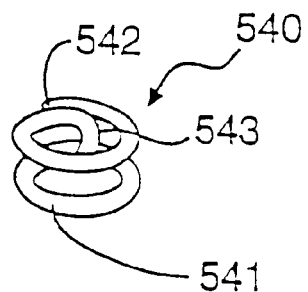
FIG. 31
FIG. 32A

METHOD AND APPARATUS FOR THE SURGICAL REPAIR OF ANEURYSMS

CROSS REFERENCE TO RELATED PATENT APPLICATIONS

This application is a divisional application of utility application Ser. No. 08/896,415, filed on Jul. 18, 1997.

This application claims priority to U.S. Provisional Application Ser. No. 60/051,209 entitled "METHOD AND APPARATUS FOR THE SURGICAL REPAIR OF ANEURYSMS" filed on Jun. 30, 1997.

BACKGROUND OF THE INVENTION

1. Field of the Invention

The present invention relates to methods and apparatus for the repair of abdominal aortic aneurysms using a novel prosthetic tube graft within the abdominal aorta.

2. Description of Related Art

An aneurysm is a ballooning of the wall of an artery resulting from the weakening of the artery due to disease or other conditions. Left untreated, the aneurysm will frequently rupture, resulting in loss of blood through the rupture and death.

Aortic aneurysms are the most common form of arterial aneurysm and are life threatening. The aorta is the main artery which supplies blood to the circulatory system. The aorta arises from the left ventricle of the heart, passes upward and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of the abdominal aorta is particularly susceptible to weakening, resulting in an aortic aneurysm. Such an aneurysm is often located near the iliac arteries. An aortic aneurysm larger than about 5 cm in diameter in this section of the aorta is ominous. Left untreated, the aneurysm may rupture, resulting in rapid, and usually fatal, hemorrhaging. Typically, a surgical procedure is not performed on aneurysms smaller than 5 cm because no statistical benefit exists in performing such procedures.

Aneurysms in the abdominal aorta are associated with a particularly high mortality rate; as accordingly, current medical standards call for urgent operative repair. Abdominal surgery, however, results in substantial stress to the body. Although the mortality rate for an aortic aneurysm is extremely high, there is also considerable mortality and morbidity associated with open surgical intervention to repair an aortic aneurysm. This intervention involves penetrating the abdominal wall to the location of the aneurysm to reinforce or replace the diseased section of the aortic aneurysm. A prosthetic device, typically a synthetic tube graft, is used for this purpose. The graft serves to exclude the aneurysm from the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Further, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, methods have been developed to attempt to treat an aortic aneurysm without the attendant risks of intra-abdominal surgical intervention. Among them are inventions disclosed and claimed in Kornberg, U.S. Pat. No. 4,562,596 for Aortic Graft, Device and Method for Performing an Intraluminal Abdominal Aortic Aneurysm Repair; Lazarus, U.S. Pat. No. 4,787,899 for Intraluminal Graft Device, System and Method; and Taheri, U.S. Pat. No. 5,042,707 for Intravascular Stapler, and Method of Operating Same.

Kornbergg discloses an aortic graft comprising a flexible tubular material having a plurality of struts to lend the graft stability and resiliency. The struts have angled hooks with barbs at their upper ends which are securely attached to the inside of the aorta above the aneurysm. Kornberg's graft is inserted using a tubular device also disclosed in his patent. Kornbergg, however, only anchors the proximal end of the graft. Kornbergg claims that the downward flow of blood holds the distal graft securely in place, so that no mechanical attachment is necessary distally. The blood pressure in the abdominal aorta, however, is typically in the magnitude of 130 mm of mercury (Hg). In spite of the direction of flow of blood through the graft, proximal to distal, substantial back pressure within the aneurysm will result unless the distal end is also mechanically attached to the aorta in a manner that prevents substantial leakage of blood between the graft and the aorta. Without distal attachment, the device of Kornbergg will not effectively exclude the weakened arterial wall at the site of the aneurysm from the forces and stress associated with the blood pressure.

Lazarus discloses a grafting system that employs a plurality of staples mounted in the proximal end of the graft. Lazarus's staples are forced through the aorta wall by means of a balloon catheter. As does Kornberg, Lazarus discloses staples mounted only in the proximal end of the graft. There is no teaching or suggestion in Lazarus U.S. Pat. No. 4,787,899 as to the desirability of, let alone means for, mechanically attaching the graft to the distal aorta below the level of the aneurysm.

Taheri discloses an articulatable stapler for implanting a graft in a blood vessel. The stapler is in the form of an elongated catheter with a plurality of segments mounted on the distal end of the catheter. The segments have beveled faces and are connected to each other by hinges. A stylet runs through the catheter to the most distal segment. The most distal segment is moved, in conjunction with the other segments, into a firing position that is substantially perpendicular to the main catheter body by the action of pulling on the stylet. The staple is implanted by using two other stylets which act as fingers to bend the staple into its attachment position.

Taheri, however, appears to be a single-fire design which can only implant one staple at a time. After each stapler is implanted, Taheri's design apparently requires that the catheter be removed before another staple is loaded. In addition, Taheri's does not teach or suggest an appropriate density of staples to secure a graft against the pulsatile blood flow of the aorta. Pressures within the aorta range from 120 mm Hg pressure to 200 mm Hg pressure. Without adequate attachment, the graft may leak around the edges continuing to allow life threatening pressures to develop in the aneurysm, and may not even remain in place.

Hence, although in recent years certain techniques have been developed that may reduce the stress, morbidity, and risk of mortality associated with surgical intervention to repair aortic aneurysms, none of the systems that have been developed effectively treat the aneurysm and exclude the affected section of aorta from the pressures and stresses associated with circulation. None of the devices disclosed in the references provide a reliable and quick means to reinforce an aneurysmal artery. In addition, all of the prior references require a sufficiently large section of healthy aorta surrounding the aneurysm to ensure attachment of the graft. The neck of the aorta at the cephalad end (i.e., above the aneurysm) is usually sufficient to maintain a graft's attachment means. However, when an aneurysm is located near the iliac arteries, there may be an ill-defined neck or no neck below the aneurysm. Such an ill-defined neck would have an insufficient amount of healthy aortic tissue to which to successfully mount a graft. Furthermore, much of the abdominal aorta wall may be calcified which may make it extremely difficult to attach the graft to the wall.

There are a number of shortcomings with the presently available graft products and their fixation within the abdominal aorta. Although sizing of "tube" or "bifurcated" grafts is radiographically-assessed prior to surgery, it is necessary for the surgeon to have a large selection of graft lengths and diameters on hand to ensure an appropriate surgical outcome. Additional shortcomings include the placement of a "circular" profile graft with an associated fixation device within an essentially "ovoid" profile vessel and the use of attachment means which fasten only to the insubstantial, structurally compromised (diseased) intima and media levels of the vessel wall. Research has exposed yet another problem which indicates that the necks of the post-surgical aorta increase in size for approximately twelve months, regardless of whether the aneurysm experiences dimensional change. This phenomenon can result in perigraft leaks and graft migration.

There are a number of currently available scanning technologies that facilitate the pre-surgical assessment of abdominal aortic aneurysms. These include: computed tomography; magnetic resonance angiography; computed angiography; sonography including Doppler, and color flow; abdominal aortography; contrast arteriography; magnetic resonance imaging (i.e., MRI); and echocardiography. The images gained by these scanning technologies are informative, but are open to multiple interpretations as they do not provide direct viewing of the portion of the aorta to be repaired. Furthermore, the performance of the procedures for these technologies may be injurious to the patient and in other instances impractical.

OBJECTS OF THE INVENTION

It is therefore an object of the present invention to provide a new and improved method of repairing an abdominal aorta aneurysm.

It is another object of the present invention to provide an apparatus for facilitating the repair of an abdominal aneurysm.

It is another object of the present invention to provide a graft for the repair of an abdominal aneurysm.

It is an object of the present invention to provide an apparatus for the repair of the aneurysm that facilitates direct viewing of the area of the aneurysm to be repaired.

It is another object of the present invention to reduce the amount of damage to the aorta and associated vasculature while repairing the aneurysm.

It is another object of the present invention to facilitate direct viewing of the vessel wall surface to assist the medical practitioner (i.e., surgeon or interventional radiologist) in the repair of vessel.

It is an object of the present invention to exclude an aneurysm from the circulatory system.

It is an object of the present invention to create a device for the repair of an aneurysm that can, without negative consequences, navigate the vessels extending to and from the aorta.

It is another object of the present invention to localize a graft within the abdominal aorta between the proximal and distal ends of the aorta.

It is an object of the present invention to firmly fasten a graft to the adventitia of the vessel wall to prevent migration of the graft.

It is another of object of the present invention to create a device to clearly visualize the surgical site during repair of the aneurysm.

It is another object of the present invention to create a uniform universal graft that is sized for use in a range of patients.

It is another object of the present invention to create a graft whose performance is not adversely effected by post surgical dimensional changes in the aortic necks.

It is another object of the present invention to create a device for the repair of the abdominal aortic aneurysm which may in addition to the classic femoral/common iliac introduction, also may be introduced via the axillary and/or brachial artery, which has not previously been contemplated.

It is another object of the present invention to provide a seal detail within an introducer sheath device that will significantly reduce blood loss during the repair procedure.

It is another object of the present invention to provide fastener assemblies that replace sutures.

It is another object of the present invention to provide a device that is capable of on board storage of a procedure specific quantity of fasteners so that it is not necessary to remove the device to reload during the repair procedure.

It is another object of the present invention to create a graft and a device for the repair of an aneurysm that reduces the invasiveness of current surgical procedures.

It is another object of the present invention to create a graft that is not dimension dependent (i.e., diameter/length) which is adaptable to the patient environment.

SUMMARY OF THE INVENTION

The present invention is directed to an attachment assembly for securing a graft to repair a vessel having an aneurysm therein. The vessel has a proximal neck or end and a distal neck or end. The graft has a proximal end and a distal end. The attachment assembly comprises attachment means for securing the distal end of the graft to the distal end of the vessel. The attachment assembly also comprises graft attachment means for securing the distal end of the graft to the attachment means. The attachment means permits expansion of the vessel necks and/or ends without negatively impacting the connection between the graft and the vessel wall. The attachment assembly may comprise a radially extending cuff. The attachment means may comprise at least one graft attachment tube for receiving the distal end of the graft. The attachment assembly is preferably formed from a flexible material.

The present invention is also directed to a repair graft assembly for repairing a vessel having an aneurysm therein.

The repair graft assembly comprises a graft assembly for creating a passageway within the vessel to reinforce the aneurysm. The graft assembly has a proximal end and a distal end. The repair graft assembly also comprises an attachment assembly. The attachment assembly comprises attachment means for securing the distal end of the graft to the distal end of the vessel. The attachment assembly also comprises graft attachment means for securing the distal end of the graft to the attachment means. The attachment means permits expansion of the vessel without negatively impacting the connection between the distal end of the graft and the vessel. The attachment assembly may comprise a radially extending cuff. The attachment means may comprise at least one graft attachment tube for receiving the distal end of the graft. The repair graft assembly is preferably formed from a flexible material. The attachment means of the repair graft assembly preferably comprises at least one graft attachment tube for receiving the distal end of the graft assembly.

The repair graft assembly comprises proximal attachment means for securing the proximal end of the graft to the proximal neck or end of the vessel. The proximal attachment means comprises a radially extending cuff.

The present invention is also directed to a visualization apparatus for viewing the interior of a vessel prior to, during and following a surgical procedure. The visualization apparatus comprises a housing and image creating means for creating an image of the interior of the vessel from within the vessel. The image creating means is located within the housing. The image creating means comprises illumination means for illuminating an area within the vessel for viewing by a user. The image creating means also comprises diverting means for temporarily diverting blood away from the viewing area. The image creating means also comprises optical viewing means for viewing the area within the vessel.

The illumination means may comprise at least one optical fiber for illuminating the area within the vessel.

The visualization means comprises means for supplying a fluid to the area to direct the flow of blood away from the viewing area, and return means for draining the fluid from the area to permit the return of blood.

The optical viewing means comprises an optical fiber. The optical viewing means may alternatively comprise scanning means for scanning an area of the vessel for creating a non optical image of the area. The scanning means may produce an ultrasound image. The scanning means may comprise a scanning catheter.

The present invention is also directed to a penetration apparatus for use in creating a plurality of treatment specific holes in the sometimes calcified vessel wall to aid in the attachment of a graft. The penetration apparatus comprises a housing, and penetration means for use in creating a plurality of treatment specific holes in the sometimes calcified vessel wall. The penetration means is located within the housing. The penetration means may comprise a laser. The laser may be an acousto optical laser or a Holmium-Yag laser. Alternatively, the penetration means may comprise a piezoelectric penetrating device. The penetration apparatus may also comprise insertion means for inserting a fastener through the opening in the vessel to secure a surgical component (e.g., graft and prosthesis) to the vessel. The penetration apparatus may also comprise secondary penetration means for forming at least one opening adjacent the opening in the sometimes calcified vessel wall. The secondary penetration means may comprise a laser or piezoelectric device. The secondary penetration means stabilizes the penetration apparatus as the insertion means inserts a fastener in the opening. The penetration apparatus may further comprise visual tracking means for identifying the location of the penetration apparatus within the vessel.

The present invention is also directed to repair apparatus for repairing a vessel during a surgical procedure. The apparatus comprises a housing and at least one of a penetration apparatus for use in forming an opening in a vessel having a calcified portion and a visualization apparatus for viewing an interior of a vessel during a surgical procedure. The penetration apparatus comprises a penetration housing, and penetration means for forming treatment specific holes in the sometimes calcified vessel wall. The visualization apparatus comprises a visualization housing, and image creating means for creating an image of the interior of the vessel from within the vessel.

The present invention is also directed to a fastener for use in a surgical procedure for securing a surgical component to a vessel. The fastener comprises fastening means for securing the surgical component to the vessel under a compressive force. The fastening means is either a wire fabrication or a coil spring fabrication.

The present invention is also directed to an introducer sheath device for use during a surgical procedure for introducing surgical components into a vessel. The introducer sheath device comprises a housing having a passageway that permits the passage of the surgical components therein. The introducer sheath device also comprises sealing means at the proximal end for preventing the loss of blood from the vessel during the insertion and subsequent removal of surgical components during the surgical procedure. The sealing means comprises a sealing cavity. The sealing cavity is filled with a sealing material, which forms a seal around the surgical components as they are inserted and removed from the introducer sheath device during the surgical procedure. The introducer sheath device further comprises positioning means for maintaining the position of the introducer sheath device within the vessel. The positioning means preferably comprises an inflatable cuff positioned at the distal end of the introducer sheath device.

BRIEF DESCRIPTION OF THE DRAWINGS

The invention will now be described in conjunction with the following drawings in which like reference numerals designate like elements and wherein:

FIGS. 21 and 22 are perspective views of an IntraVascular UltraSound (IVUS) based repair apparatus according to another embodiment of the present invention containing a visualization device and a penetration device;

FIGS. 29 and 30 are perspective views of a wire fastener according to another embodiment of the present invention for securing the cuff detail of a surgical cuff to a vessel wall;

FIGS. 31, 32a, 32b, 32c, 32d and 32e are perspective views of a fastener according to another embodiment of the present invention for securing the cuff to a vessel wall;

DETAILED DESCRIPTION OF PREFERRED EMBODIMENTS

The following descriptions of the preferred embodiments of the present invention are described, for purpose of example, in connection with the repair of an abdominal aortic aneurysm. The inventors of the present subject matter contemplate that the embodiments described herein are capable of use in the repair of other vessels and in other procedures. Thus, it is intended that the present invention cover the modifications and variations of the invention, provided they come within the scope of the appended claims and their equivalents.

Repair Graft

Reference will now be made in detail to preferred embodiments of grafts according to the present invention for repair of abdominal aortic aneurysms, an example of which is illustrated in FIGS. 1–9.

Figure 1A:
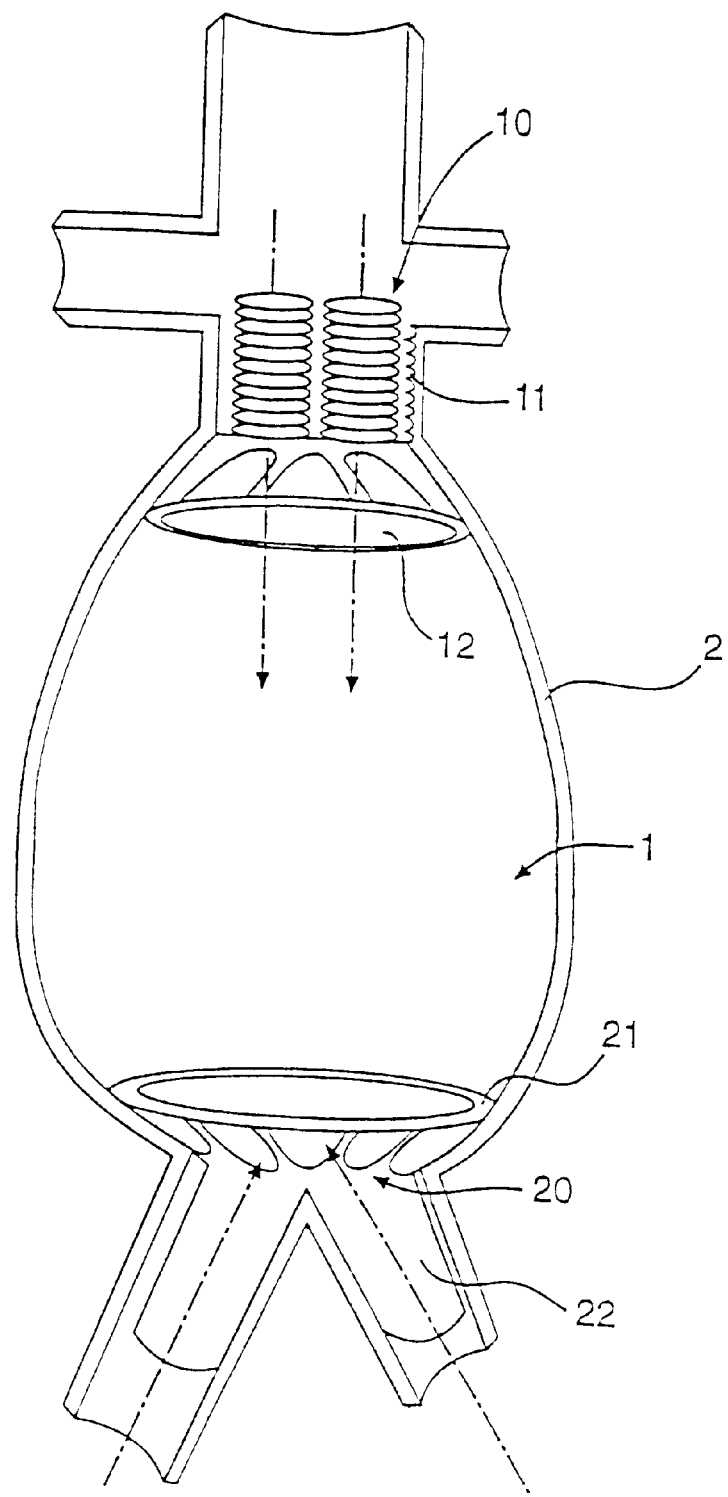
FIG. 1A is a perspective view of a prosthetic bifurcated tube graft and bifurcated cuff according to a preferred embodiment of the present invention.
Figure 2A:
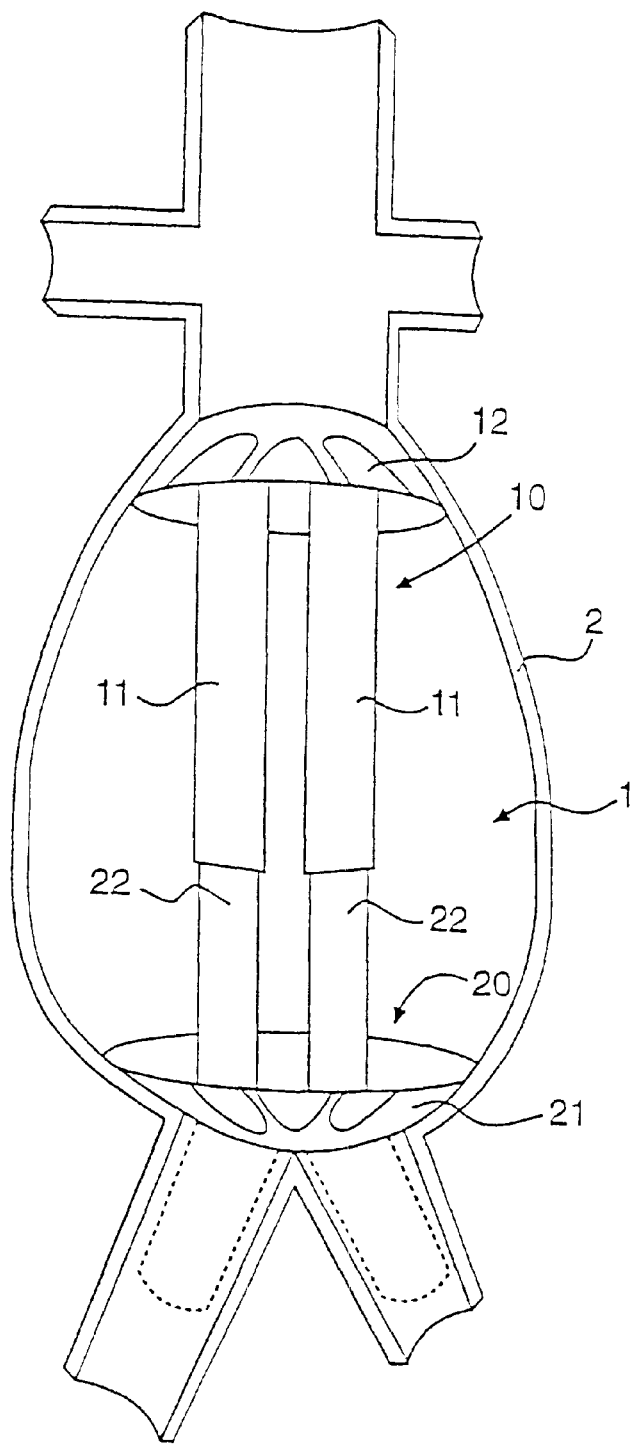
FIG. 2A is a perspective view of the prosthetic bifurcated tube graft and bifurcated cuff of FIG. 1A secured within the abdominal aorta.

FIGS. 1A and 2A depict a preferred embodiment of the repair graft assembly of the present invention directed to a proximal graft assembly 10 and distal graft assembly 20 for repair of a vessel 1. The proximal graft assembly 10 and distal graft assembly 20 are secured to a wall 2 of the vessel 1 to exclude the aneurysm from the circulatory system of the patient. In the preferred embodiment of the present invention, the proximal graft assembly 10 is a bifurcated tube graft.

The distal graft assembly 20 preferably comprises an attachment cuff 21. The attachment cuff 21 is sized to secure the distal graft assembly 20 to the wall 2 of the vessel 1 at the distal end of the vessel 1. The distal graft assembly 20 also comprises at least one graft attachment leg, tube or branch 22. The attachment cuff 21 is secured to the wall 2 of the vessel 1 out to the adventitia using a suitable fastener, described in detail below.

Figure 5:
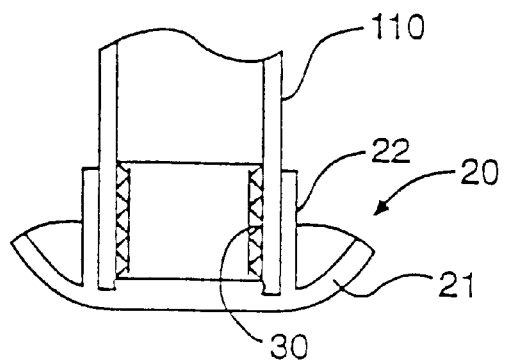
FIG. 5 is a perspective view of the connection between the prosthetic tube graft and the cuff.

The distal graft assembly 20 is positioned within the distal end of the vessel 1, as shown in FIG. 1A using a guide wire, not shown, that extends between and through both common iliacs. The attachment cuff 21 is then secured to distal end of the vessel 1 out to the adventitia using a repair apparatus, described below. After the attachment cuff 21 is firmly secured to the wall 2, attachment tubes 22 are invaginated to the position shown in FIG. 2A. A proximal graft assembly 10 is then secured to the attachment legs 22 using suitable connectors, such as, a self-expanding stent 30, as shown in FIG. 5.

The bifurcated proximal graft assembly 10 comprises a pair of tubular legs 11. The tubular legs 11 are sized to be received within/without the graft attachment tubes 22. The bifurcated proximal graft assembly 10 may also comprise an attachment cuff 12 for attachment to the wall 2 of the vessel 1. The attachment cuff 12 has a similar structure to the attachment cuff 21 of attachment device 20. The tubular legs 11 are invaginated following the process of securing the attachment cuff 12 to the wall 2. The attachment legs 22 may be positioned within the tubular legs 11, as shown in FIG. 2A. Alternatively, the tubular legs 11 may be positioned within the attachment legs 22, as shown in the embodiment of FIG. 4.

Figure 1B:
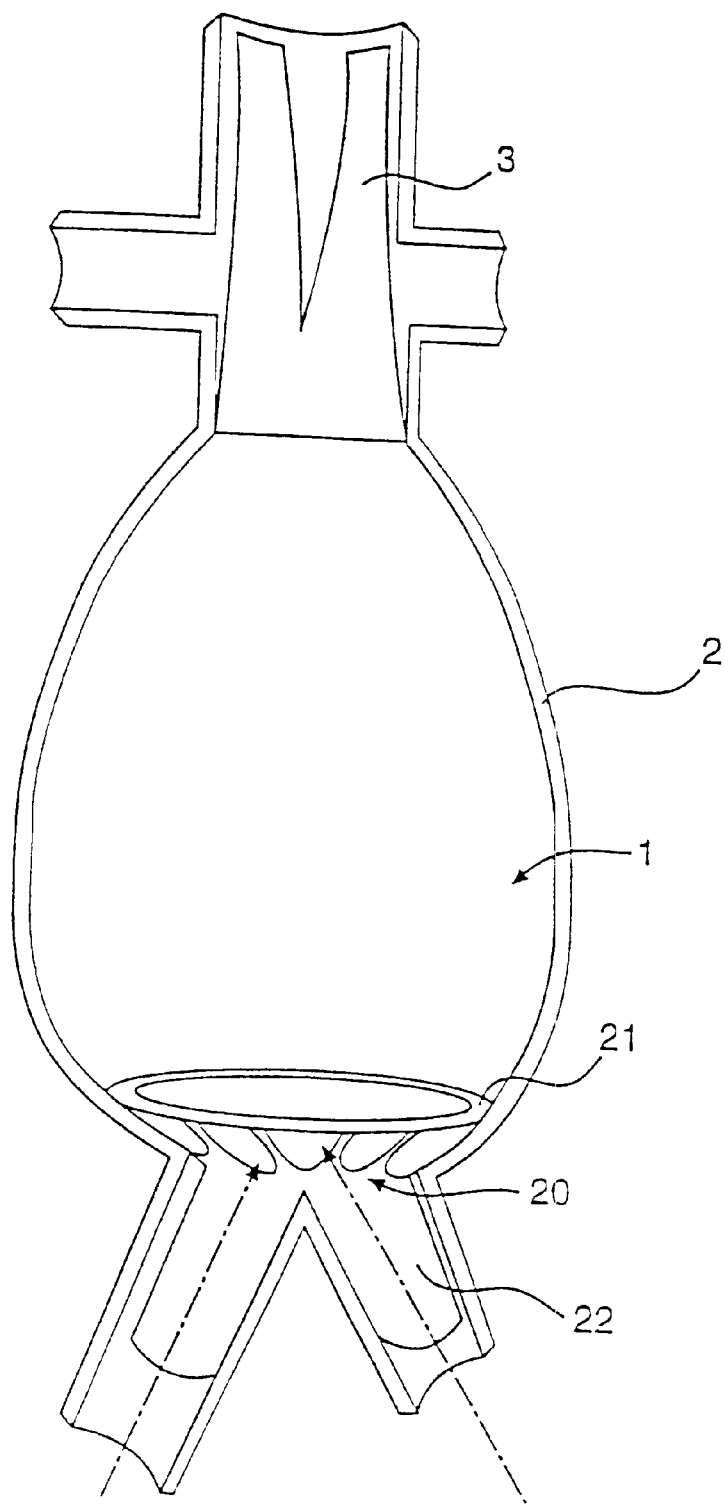
FIG. 1B is a perspective view of a prosthetic bifurcated tube graft and bifurcated cuff according to another embodiment of the present invention.
Figure 2B:
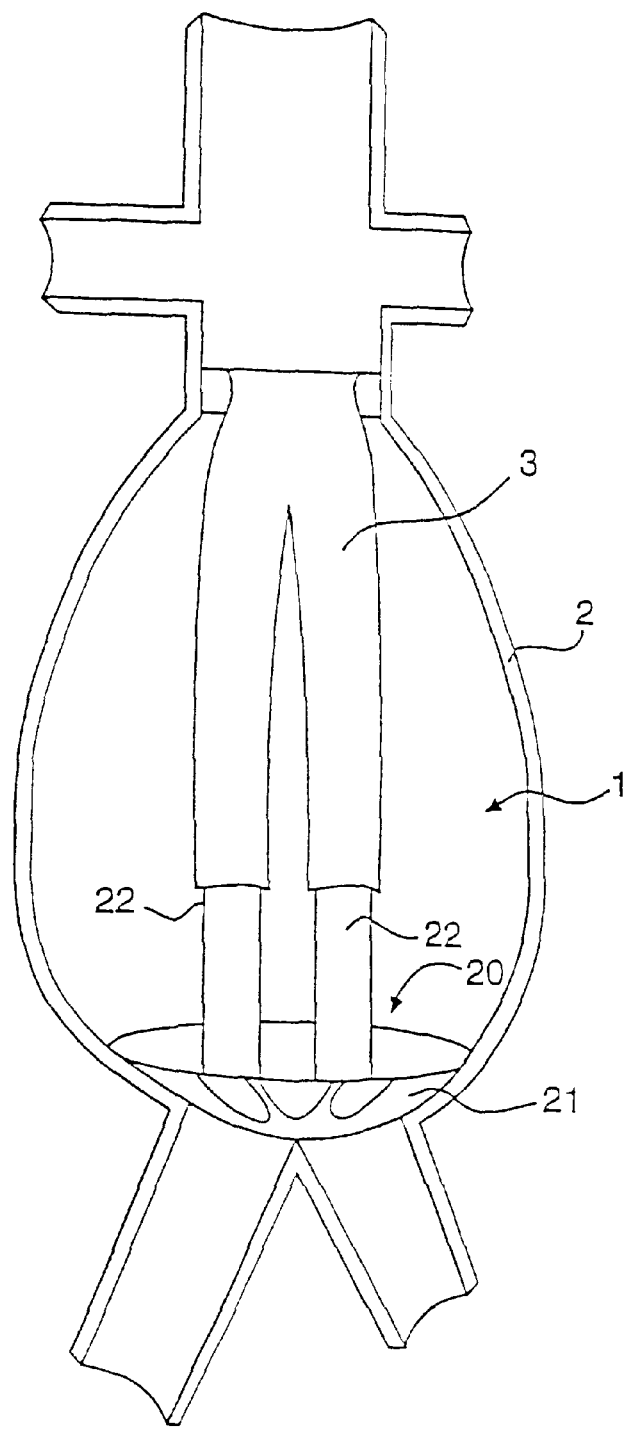
FIG. 2B is a perspective view of the prosthetic bifurcated tube graft and bifurcated cuff of FIG. 1B secured within the abdominal aorta.

It is also contemplated that the distal graft assembly 20 may be used with a standard tube graft 3, as shown in FIG. 1B and 2B. In this variation, the tube graft 3 is secured to the wall 2 of the vessel 1 while in an inverted position, as shown in FIG. 1B using fasteners, described below, and a self-expanding stent 30, if desired. The tube graft 3 is then invaginated and secured to the distal graft assembly 20, as described above. The benefit of the invagination of the graft 3 is that the fasteners securing the graft 3 to the vessel 1 are not in direct contact with the blood within the vessel 1. This will reduce the possible build up of thrombus at the point of attachment and thereafater the creation of emboli.

The proximal graft assembly 10 and distal graft assembly 20 will enable the creation of a cross sectional area ratio between the common iliacs and the distal aorta that exists only at childhood. The ratio may be 1.1 to 1.0. This ratio minimizes the reflected wave that is instrumental in the creation of plaque deposits at the distal bifurcation.

Figure 3:
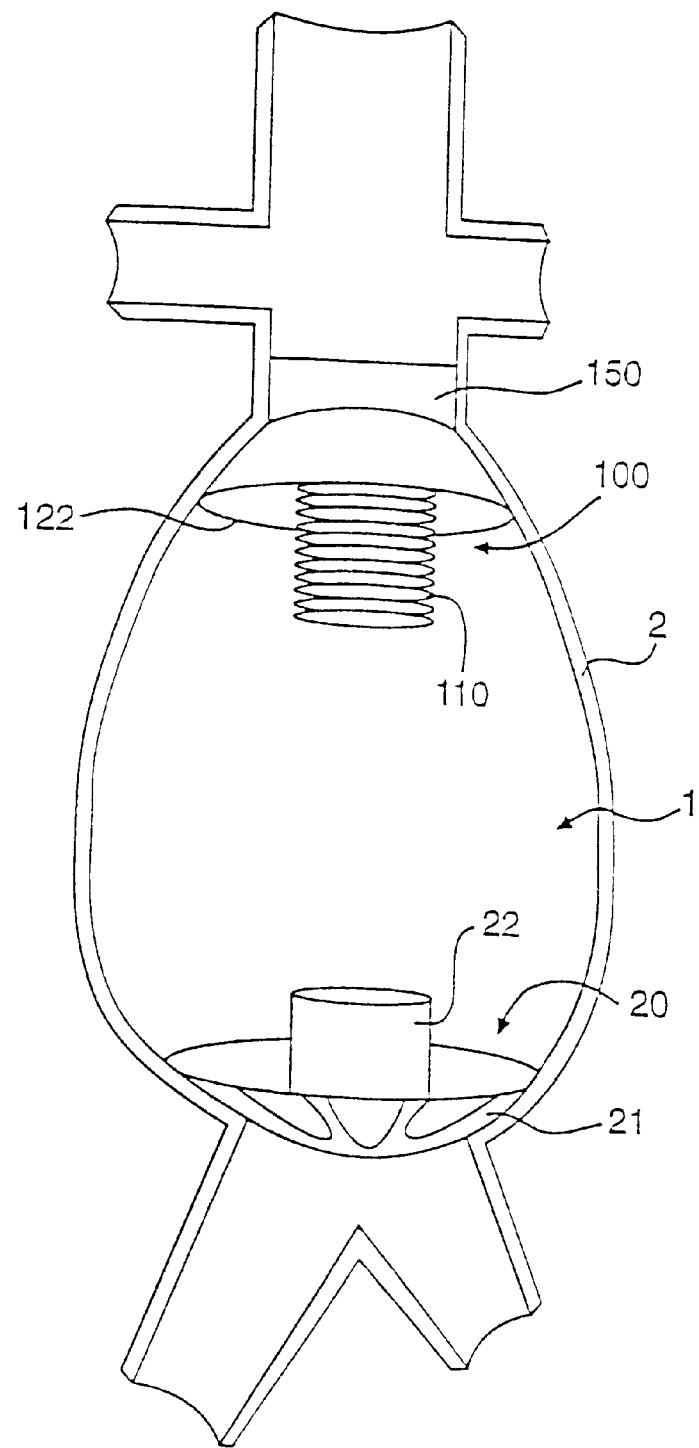
FIG. 3 is a perspective view of a prosthetic tube graft and cuff according to another embodiment of the present invention.
Figure 4:
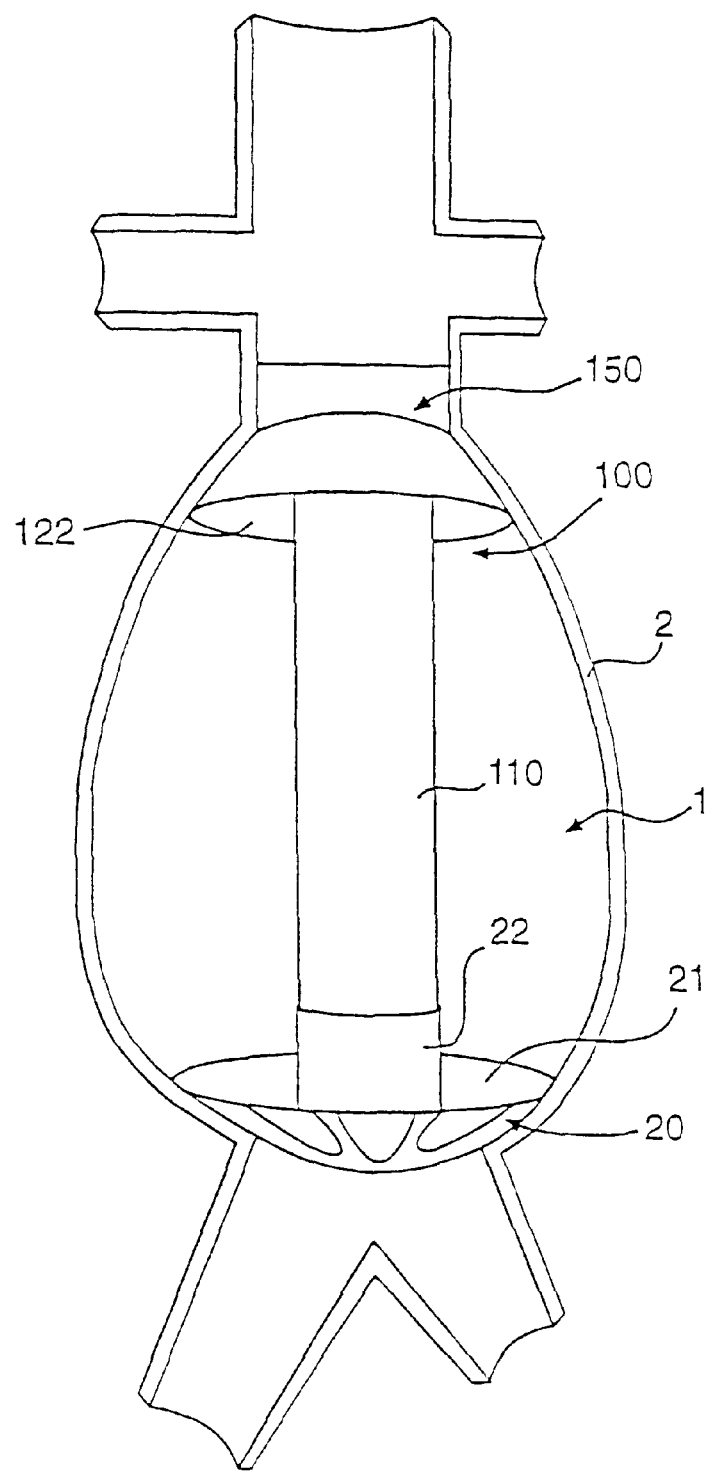
FIG. 4 is a perspective view of the prosthetic tube graft and cuff of FIG. 3 secured within the abdominal aorta.

FIGS. 3 and 4 depict another embodiment of a repair graft for repair of an abdominal aortic aneurysm or vessel 1 according to the present invention. The proximal graft assembly 100 is secured to a wall 2 of the abdominal aorta to exclude the vessel 1 from the circulatory system of the patient. The proximal graft assembly 100 is used in connection with the distal graft assembly 20, described above. In this embodiment, the distal graft assembly 20 comprises a single attachment leg or tube 22. The proximal graft assembly 100 comprises a tube graft assembly 110 for forming a passageway within the vessel 1.

Figure 9:
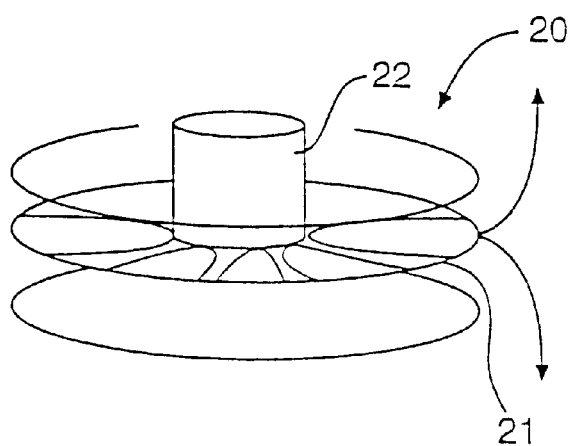
FIG. 9 is a perspective view of the flexible attachment cuff according to embodiments of the present invention.

The radially extending attachment cuff 122 provides a greater surface area for securing the proximal graft assembly 100 to the wall 2. Additionally, the radially extending portion 122 is flexible, which permits some positioning adjustment of the proximal graft assembly 100 in the event the size of the passageway within the abdominal aorta changes after the surgical procedure. FIG. 9 illustrates the flexibility of the attachment cuff 21 which is similar to attachment cuff 122. Like the embodiment of FIGS. 1A and 2A, the proximal graft assembly 100 is secured to the vessel wall 2 in an invaginated manner, as shown in FIG. 3. After the attachment cuff 122 is secured to the vessel wall 2, the proximal graft assembly 100 is invaginated to the position shown in FIG. 4. The tubular leg assembly 110 is then secured to the distal graft assembly 20, as shown in FIG. 5. In a preferred embodiment, a self-expanding stent 30 is used to secure it to the attachment leg 22 of the distal graft assembly 20. The self-expanding stent 30 applies radial pressure against an inner surface of tube graft assembly 110 to secure the tube graft assembly 110 to the distal graft assembly 20.

The self-expanding stent 30 is a preferred method of securing the proximal tube assemblies 10 or 100 to the distal graft assembly 20. However, it will be apparent to those skilled in the art that various modifications and variations can be made in the construction and configuration of the present invention without departing from the scope or spirit of the invention. For example, surgical staples, sutures, adhesives or other methods may be used to secure the proximal graft assembly 10 to the distal graft assembly 20. Thus, it is intended that the present invention cover the modifications and variations of the invention, provided they fall within the scope of the appended claims and their equivalents.

As described above in connection with FIGS. 1B and 2B, it is also contemplated that the distal graft assembly 20 may be used with a standard tube graft, not shown. The tube graft will also be secured to the wall 2 of the vessel 1 while in a cephalad position using either fastener devices, described below, or a self-expanding stent 30. The tube graft is then invaginated and secured to the distal graft assembly 20, as described above.

Figure 6:
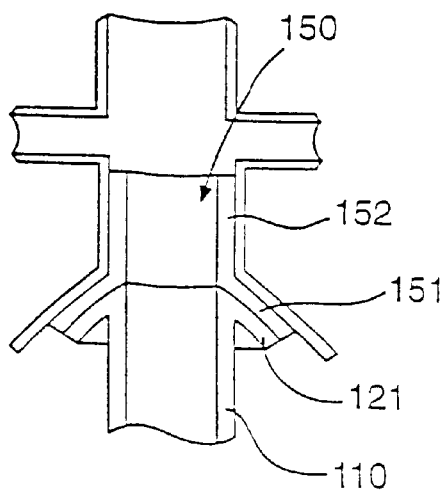
FIG. 6 is a side view of the prosthetic tube graft of FIG. 4 secured to a secondary cuff.
Figure 7:
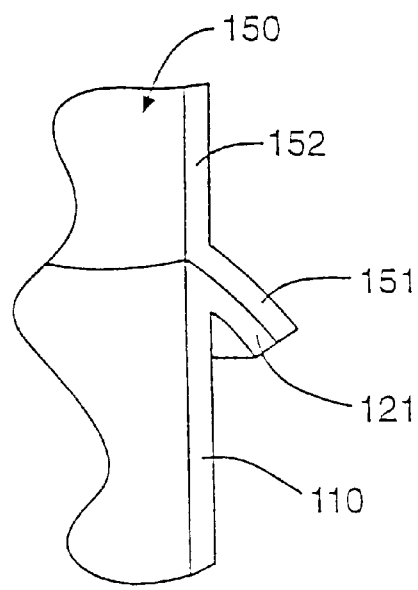
FIG. 7 is an exploded view of the connection between the prosthetic tube graft and secondary cuff as shown in FIG. 6.

FIGS. 6 and 7 depict a proximal attachment assembly 150 according to the present invention for securing the proximal graft assembly 10 or 100 to the proximal end of the vessel 1. It is preferred that the proximal attachment assembly 150 be used in connection with securing the proximal graft assemblies 10 or 100 to the vessel wall 2 according to preferred embodiments of the present invention as shown, for example, in FIGS. 3, 4, 6 and 7. The proximal attachment assembly 150 comprises a cuff attachment portion 151 and a vessel attachment portion 152. The attachment cuff 12 or 121 is secured to the cuff attachment portion 151, by sewing, for example. The vessel attachment portion 151 is then secured to the vessel 1 using, for example, a fastener or a self-expanding stent 30 and fasteners, if necessary. Alternatively, the proximal attachment assembly 150 may be invaginated and secured to the vessel 1 in the manner described above in connection with FIGS. 1B and 2B. The cuff attachment portion 151 and the attachment cuff 12 or 121 interact in a manner such that the proximal graft assembly 10 or 100 are not impacted by the expansion of the neck of vessel 1 after the surgical procedure.

Figure 8:
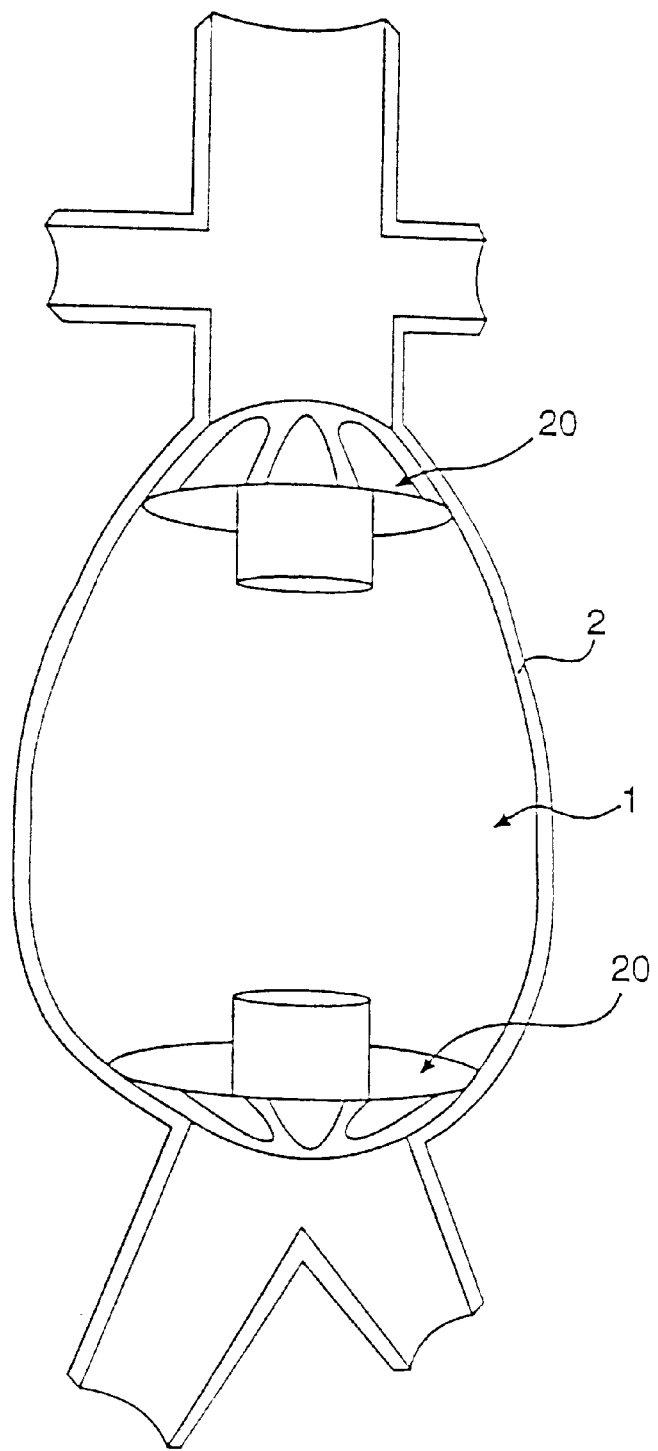
FIG. 8 is a perspective view of attachment cuffs according to another embodiment of the present invention.
Figure 10:
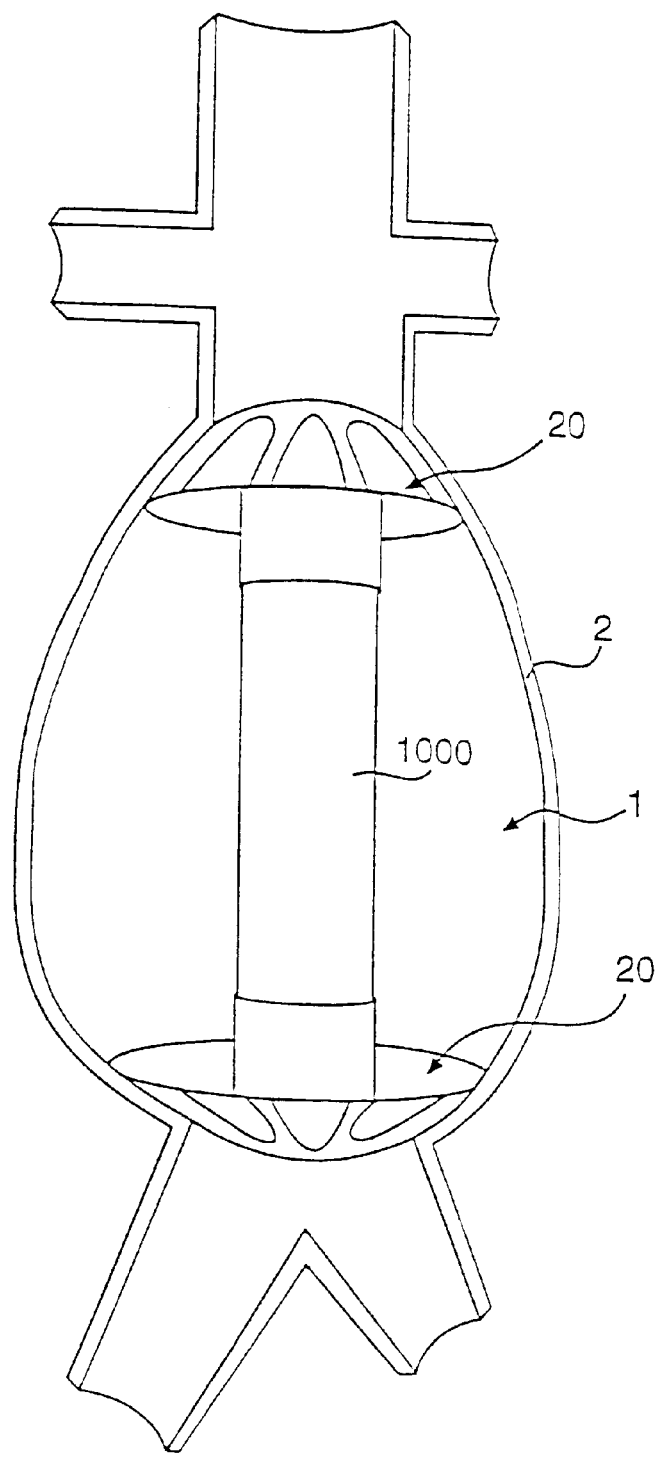
FIG. 10 is a perspective view of the attachment cuffs of FIG. 8 having a prosthetic tube graft secured between the attachment cuffs.

Another embodiment of the repair grafts according to the present invention are disclosed in FIGS. 8 and 10. The embodiment of FIGS. 8 and 10 utilizes a pair of distal graft assemblies 20, which are secured at the proximal and distal ends of the vessel. A proximal graft assembly 1000, which forms a passageway within the vessel 1 interconnects the distal graft assemblies 20. As described above, the proximal graft assembly 1000 is secured to the attachment legs 22 of the distal graft assemblies 20 using a self-expanding stent 30 or other suitable fastening means. The attachment legs 22 may be inserted in the proximal graft assembly 1000. Alternatively, the proximal graft assembly 1000 may be inserted in the attachment legs 22, as shown in FIG. 10.

The above described repair grafts facilitates repair of a vessel in a manner that is neither profile nor dimension dependent. This is especially helpful in view of the fact that the necks of the post-surgical aorta typically increases in size for approximately twelve months. The above-described repair grafts accommodate such expansion without allowing leaks or graft migration. The attachment cuffs are capable of accommodating dimensional changes in the necks of the abdominal aorta. Furthermore, the use of the distal graft assembly, 20 permits distal attachment removing the need for iliac/femoral attachment In the above described embodiments, the proximal graft assemblies 10, 100 and 1000, distal graft assembly, and proximal attachment assembly 150 are preferably formed from Gore-Tex® or equivalent biocompatible material. It will be apparent to those skilled in the art that various modifications and variations can be made in the construction and configuration of the present invention without departing from the scope or spirit of the invention. For example, in the embodiments mentioned above, various other suitable materials such as, Dacron®, and other biocompatible graft materials may be used to form the repair grafts. Thus, it is intended that the present invention cover the modifications and variations of the invention, provided they fall within the scope of the appended claims and their equivalents.

Similar to other graft procedures, the proximal graft assemblies 10, 100, or 1000 according to the present invention require attachment to the wall 2 of the vessel. Often, it is necessary to attach the distal end of the graft into material which is routinely calcified and therefore difficult to penetrate. When paired with the absence of a distal neck in the vessel, the presence of the plaque has forced others to promote the use of a bifurcated graft in which the graft limbs are fastened by stents within the common iliac or femoral arteries. This procedure may potentially damage the femoral arteries. Furthermore, the presence of a graft and stent within the iliac or femoral arteries potentially restricts the flow of blood within the vessels. This is unnecessary when utilizing the repair grafts according to the present invention.

IntraVascular Endoscopy (IVE) Based Repair System

Reference will now be made in detail to preferred embodiments of an apparatus according to the present invention for facilitating the repair of abdominal aortic aneurysms using above described grafts. An example of an intravascular endoscopy based system is depicted in FIGS. 11–17.

Figure 12:
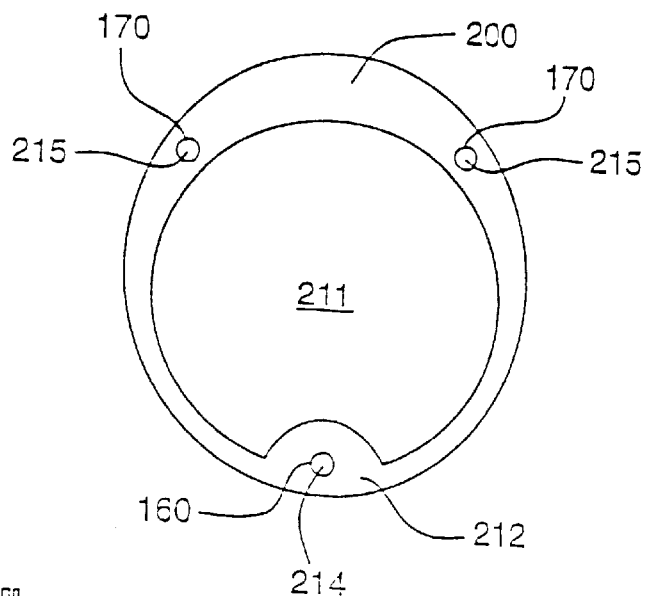
FIG. 12 is an end view of the IntraVascular Endoscopy (IVE) based repair system according to the embodiment of FIG. 11.
Figure 15A:
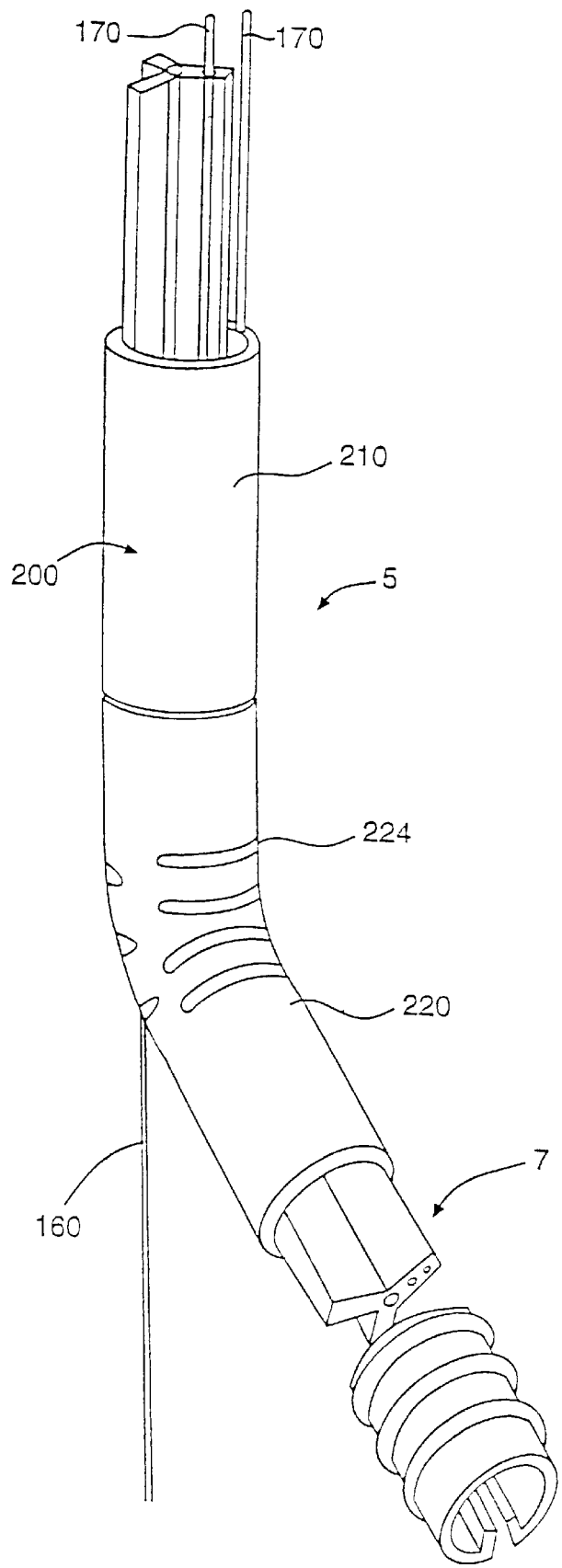
FIG. 15A is a perspective view of an IntraVascular Endoscopy (IVE) based repair system according to an embodiment of the present invention containing an embodiment of a penetration device according to the present invention and an embodiment of a fastener cartridge according to the present invention.
Figure 15B:
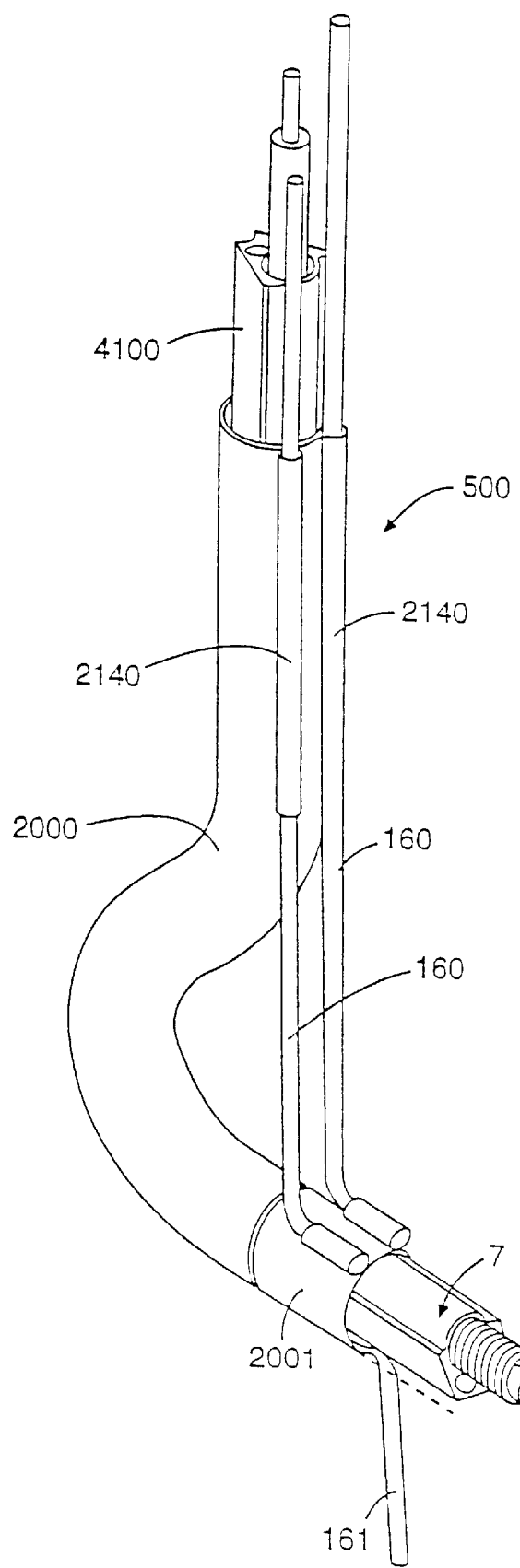
FIG. 15B is a perspective view of an IVE based repair system according to another embodiment of the present invention containing a penetration device and fastener cartridge according to the present invention.
Figure 15C:
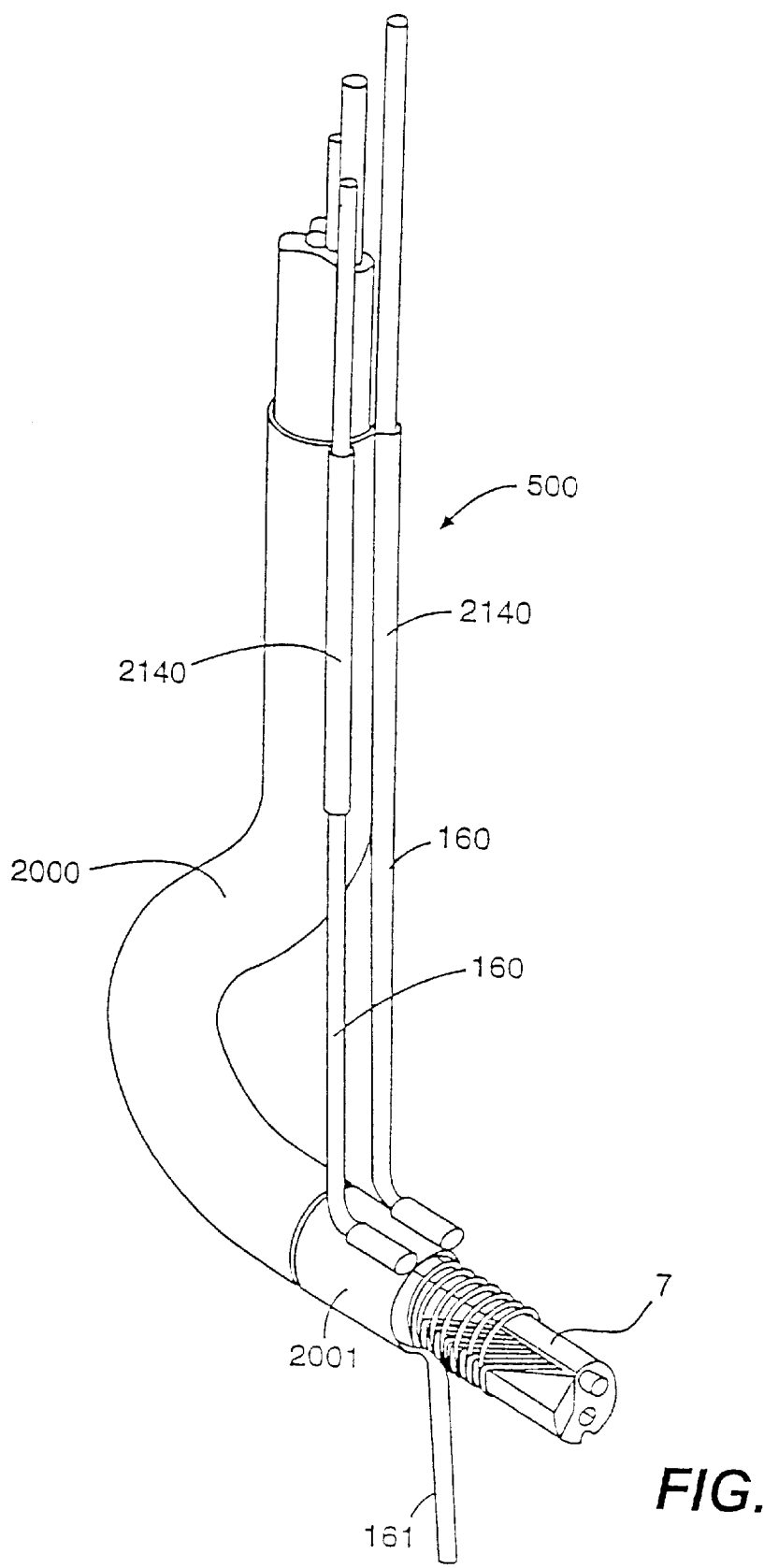
FIG. 15C is a perspective view of an IVE based repair system according to the embodiment of FIG. 15B containing a penetration device and fastener cartridge according to another embodiment of the present invention.
Figure 15D:
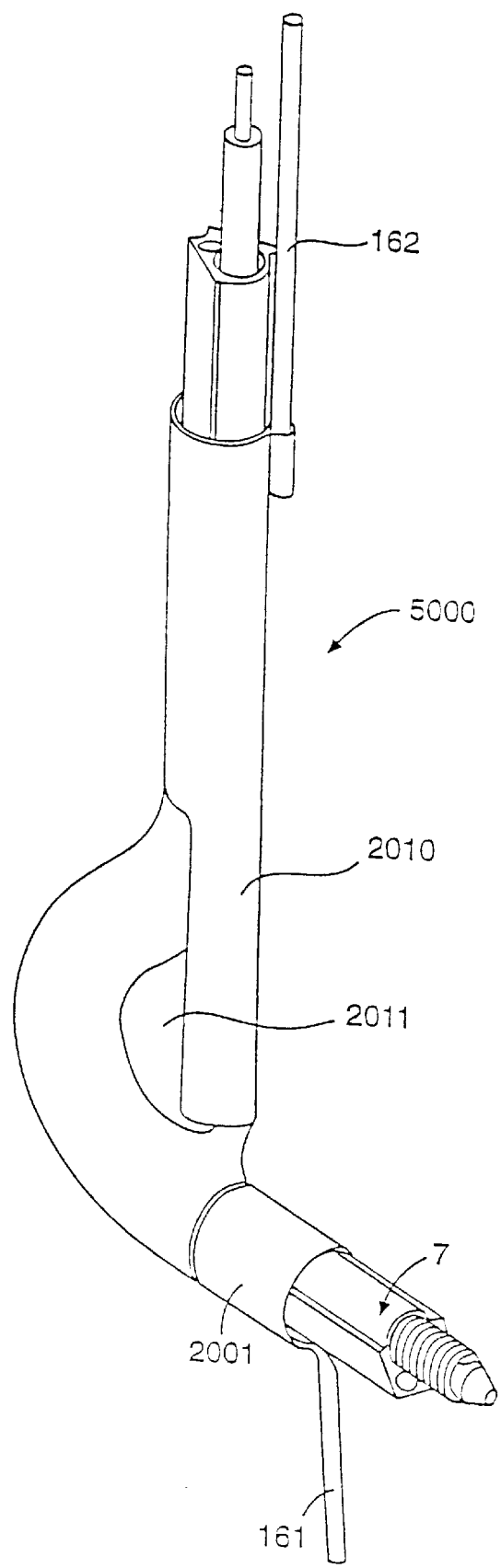
FIG. 15D is a perspective view of an IVE based repair system according to another embodiment of the present invention containing a penetration device and fastener cartridge according to the present invention.

The repair apparatus 5 comprises a housing 200 for alternately receiving a visualization apparatus 6 and a penetration apparatus 7, as shown in FIG. 15D. It, however, is contemplated by the inventors of the present invention that the visualization apparatus 6 and penetration apparatus 7 may be combined into a single assembly within the repair apparatus 5. The housing 200 has a hollow construction, as illustrated in FIG. 12, which permits insertion of the visualization apparatus 6 or the penetration apparatus 7, described in detail below. The housing 200 is divided into two primary portions: static housing portion 210; and flexible housing portion 220. The housing 200 has a sufficient length such that it extends from the repair site within the vessel 1 through the appropriate or chosen artery to a point outside the patient.

The housing 200 has a hollow interior 211 to permit passage of one of the interchangeable apparatus 6 and 7. An inner surface of the hollow interior 211 comprises rotation prevention means 212 for properly orienting the interchangeable apparatus 6 and 7 within the housing 200. In a preferred embodiment, the rotation prevention means 212 is a ridge, as shown in FIG. 12, that extends along the inner surface of the hollow interior 211. It, however, will be apparent to those skilled in the art that various modifications and variations can be made in the construction and configuration of the present invention without departing from the scope or spirit of the invention. For example, the rotation prevention means 211 mentioned above, may be located at different radial positions within the housing and may also be a ridge, a groove, a plurality of grooves, or other devices capable of preventing rotation of the interchangeable apparatus 6 and 7 within the housing 200. Thus, it is intended that the present invention cover the modifications and variations of the invention, provided they fall within the scope of the appended claims and their equivalents.

Figure 11:
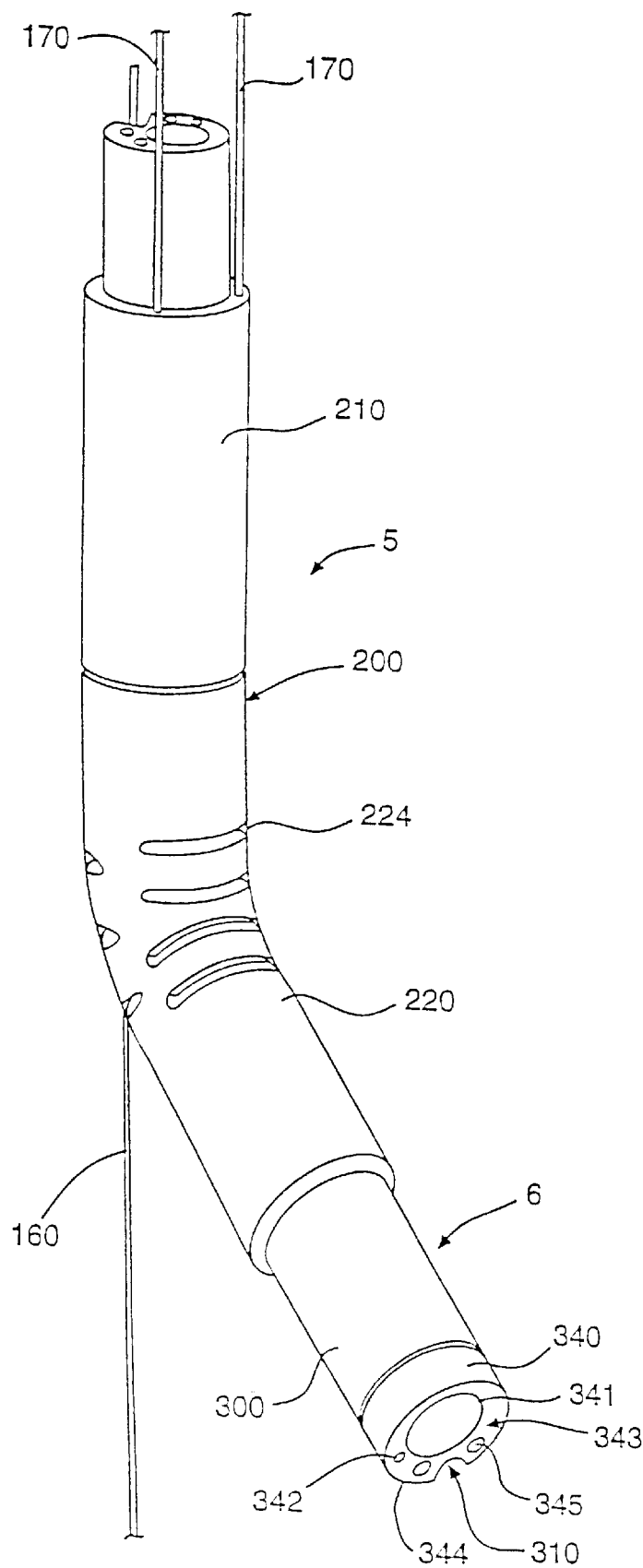
FIG. 11 is a perspective view of an IntraVascular Endoscopy (IVE) based repair system according to an embodiment of the present invention containing an embodiment of a visualization device according to the present invention.
Figure 14:
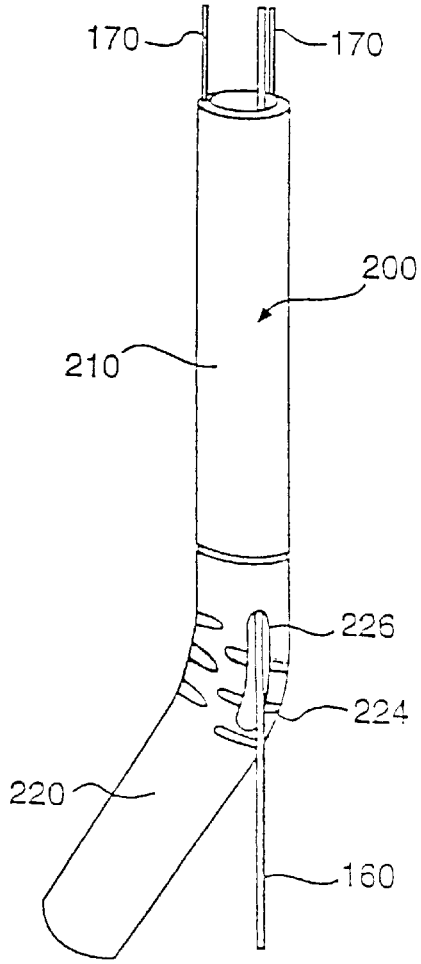
FIG. 14 is another perspective view of the IntraVascular Endoscopy (IVE) based repair system illustrating the guide wire and articulation cables exiting the housing of the repair system.

Positioned within the housing 200 is an apparatus guide means 214 for guiding the repair apparatus 5, as shown in FIGS. 11 and 15A, within the vessel 1 during use. The guide means 214 preferably is a passageway or lumen extending within the housing wall through the static portion 210. A guiding means 160 cooperates with guide means 214 to guide the apparatus 5 during use. The guiding means 160 is preferably a guide wire which is capable of extending from the femoral artery to the axillary artery. In a preferred embodiment, the guide wire 160 is a filament (e.g., stainless steel, titanium or a Kevlar®). It, however, will be apparent to those skilled in the art that various other materials having similar properties of physical integrity, high strength, flexibility, and mnimal thermal expansion may be used to form the guide wire 160. The guide wire 160 projects from the flexible housing portion 220 through an aperture 226 in the housing 200, as shown in FIG. 14.

Housing 200 also comprises an apparatus manipulation means 215 to aid in manipulating and orienting the apparatus 5 within the vessel 1 during the repair operation. The manipulation means 215 preferably comprises at least one passageway extending within the housing wall through the static housing portion 210 and terminating in the flexible housing portion 220. A manipulating means 170 cooperates with manipulation means 215 to guide the apparatus 5 during use. The manipulating means 170 is preferably comprises at least one guide wire that is capable of extending from outside the patient through the housing 200. The guide wires 170 extend through the manipulating means 215. In a preferred embodiment, the guide wires 170 are filaments (e.g., stainless steel, titanium or a Kevlar®). It, however, will be apparent to those skilled in the art that various other materials having similar properties of physical integrity, high strength and flexibility may be used to form the guide wires 170.

The guide wires of the manipulating means 170 terminate within the flexible housing portion 220. Operation of the manipulating means 170 results in the articulation of an end portion of the flexible housing portion 220. The guide wires 170 maintain the flexible housing portion 220 in an articulated position, as shown in FIGS. 11 and 14, such that the visualization apparatus 6 and the penetration apparatus 7 can be interchanged without altering the orientation of the repair apparatus 5 with respect to the surgical site.

The wall of the static housing portion 210 comprises an outer surface formed from silicone and an inner surface formed from Teflon®. It, however, will be apparent to those skilled in the art that various modifications and variations can be made in the construction and configuration of the present invention without departing from the scope or spirit of the invention. For example, the housing wall may be formed from a suitable polymer (e.g., Pebax®) or other material having similar properties including, but not limited to biocompatability, flexural strength, low coefficient of friction. Thus, it is intended that the present invention cover the modifications and variations of the invention, provided they fall within the scope of the appended claims and their equivalents.

The flexible housing portion 220 may be formed in a manner similar to static housing portion 210. For example, the housing may comprise an outer surface formed from silicon and an inner surface formed from Teflon®. It, however, will be apparent to those skilled in the art that various modifications and variations can be made in the construction and configuration of the present invention without departing from the scope or spirit of the invention. For example, the lining may be formed from a suitable polymer or other material having similar properties including, but not limited to biocompatability, flexural strength, low coefficient of friction. Alternatively, the flexible housing portion 220 may comprise a coiled metallic spring outer casing 224 that surrounds a lining. The lining may be formed from Teflon®. The coiled metallic spring outer casing 224 may be formed from a biocompatible stainless steel or titanium. Furthermore, the spring outer casing 224 may be formed from other suitable spring materials. It is not necessary that the outer spring casing 224 extend along the entire length of the flexible housing portion 220. Rather, the outer spring casing 224 may be positioned along the portion of the flexible housing portion 220 that is subject to bending. However, it is contemplated that an outer spring casing that extends along the entire length of the flexible housing portion 220 be within the scope of the present invention.

The flexible housing portion 220 and the static housing portion 210 are manufactured as separate components. It, however, will be apparent to those skilled in the art that various modifications and variations can be made in the construction and configuration of the present invention without departing from the scope or spirit of the invention. For example, the static housing portion 210 and the flexible housing portion 220 may be formed as a single component. In a preferred embodiment, the static housing portion 210 is permanently secured to the flexible housing portion 220. However, it is contemplated that the housing portions 210 and 220 may also be removably attached.

FIGS. 15B and 15C illustrates another repair apparatus 500 for alternatively receiving a visualization apparatus 6 and a penetration apparatus 7 according to another embodiment of the present invention. The repair apparatus 500 comprises a housing 2000 for alternatively receiving a visualization apparatus 6 and a penetration apparatus 7. The housing 2000 is flexible and has a sufficient length such that it extends from the repair site within the vessel 1 through the appropriate artery to a point outside the patient.

The housing 2000 is hollow, as described above in connection with housing 200, to permit passage of one of the interchangeable apparatus 6 or 7. The housing 2000 includes at least one guide means 2140 positioned at the exterior of the housing 2000 for guiding the repair apparatus 500 within the vessel 1 during use. The guide means 2140 preferably is a passageway extending along the exterior of the housing wall to a point adjacent the distal end 2001 of the housing 2000.

Guide wires 160 extend within the guide means 2140. The guide wires 160 extend from the end of guide means 2140 and are secured to the distal end 2001 of the housing 2000, as shown in FIGS. 15B and 15C. Adjustment of the guide wires 160 manipulates the position of the repair apparatus 500 within the vessel 1. The above described arrangement permits a wide range of articulation of the repair apparatus 500 within the vessel 1.

An additional guide wire 161 is secured to the distal end 2001 of the housing 2000. The guide wire 161 extends through the vessel 1 and appropriate artery to permit the positional adjustment of the repair apparatus 500 within the vessel.

FIG. 15D illustrates another repair apparatus 5000 for alternatively receiving a visualization apparatus 6 and a penetration apparatus 7 according to another embodiment of the present invention. The repair apparatus 5000 comprises a flexible hollow housing 2010 and has a sufficient length such that it extends from the repair site within the vessel 1 through the appropriate artery to a point outside.

The housing 2010 includes at least one guide wire 162 extending along the exterior of the housing 2010, as shown in FIG. 15D. The housing 2010 includes an inflatable portion 2011, located adjacent the distal end 2001. Inflation of the inflatable portion 2011 permits articulation of the repair apparatus 5000 within the vessel 1. A passageway, not shown, extends within the housing 2010 to permit inflation of the inflatable portion 2011 with a suitable fluid, such as, saline or suitable liquid polymers or air. An additional guide wire 161 is secured to the distal end 2001 of the housing 2010. The guide wire 161 extends through the vessel 1 and appropriate artery to permit the positional adjustment of the repair apparatus within the vessel.

The overall dimensions of the repair apparatus 5 allows axillary access. This previously was not possible. In this regard, the repair apparatus used in connection with the visualization apparatus 6 or penetration apparatus 7 is capable of being used in other surgical procedures not previously contemplated. The apparatus size permits insertion through an introducer sheath device 900, described below. The apparatus 5 may also be introduced into a vessel percutaneously. This procedure is less invasive and/or intrusive when compared to other repair surgical procedures.

IntraVascular Endoscopy (IVE) Visualization Apparatus

Reference will now be made in detail to preferred embodiments of the interchangeable apparatus 6 and 7 for use with the repair apparatus 5 according to the present invention for facilitating the repair of abdominal aortic aneurysms. The visualization apparatus 6 will now be described in connection with FIGS. 11 and 13.

A visualization apparatus 6 may be inserted within the repair apparatus 5 to illuminate and permit real time direct viewing of the abdominal aorta to aid and the diagnosis and repair of the aneurysm. The visualization apparatus 6 is an intravascular endoscope based system that comprises a housing 300 for housing various illuminating and viewing components. The housing 300 is preferably formed as a conduit that is sized to slide within housing 200. In a preferred embodiment, the housing 300 is an extrusion of silicon, Teflon® or polymer or other material having similar properties.

The housing 300 extends through the hollow interior 211 of the housing 200. The housing 300 may comprise orientation means 310 for orienting the visualization apparatus 6 within the housing 200. The orientation means 310 cooperates with rotation prevention means 212. In a preferred embodiment, the orientation means 310 is a channel that extends along an outer surface of the housing 300. It, however, will be apparent to those skilled in the art that various modifications and variations can be made in the construction and configuration of the present invention without departing from the scope or spirit of the invention. For example, the orientation means 310 mentioned above may be located at different radial positions within the housing 300. The orientation means 310, may be a ridge, a groove, a plurality of grooves, or other devices that are complementary with the rotation prevention means 212 to prevent rotation of the visualization apparatus 6 within the housing 200.

Figure 13:
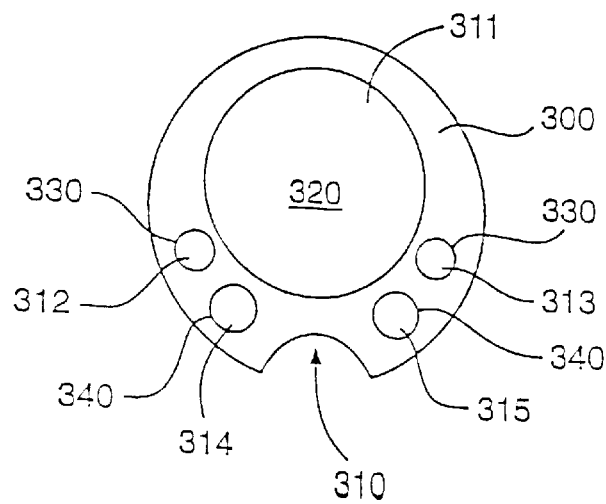
FIG. 13 is an end view of the visualization device depicted in FIG. 11.

As shown in FIG. 13, housing 300 comprises a plurality of passageways 311, 312, 313, 314, and 315 formed therein. The passageways 311, 312, 313, 314, and 315 extend along the entire length of the housing 300. Central passageway 311 is provided for the passage of optical viewing means 320 for viewing an abdominal aorta. In a preferred embodiment, the optical viewing means 320 is a fiber optic system. The system incorporates a fiber optic bundle. It, however, will be apparent to those skilled in the art that various modifications and variations can be made in the construction and configuration of the present invention without departing from the scope or spirit of the invention. For example, the optical viewing means 320 mentioned above, may be any flexible optical system that is sized for use in surgical applications. The optical viewing means 320 permits real time direct viewing of the area of repair in the vessel 1. The optical viewing means 320 may be connected to a video camera and monitor, not shown, that permits the surgeon to view the repair area. The images may be stored and recalled as desired by using either a video printer or video cassette recorder. The penetration apparatus 7 will be located at the same position as the visualization apparatus 6. The penetration apparatus 7 incorporates a radio opaque marker that will indicate the precise position of the penetration apparatus 7 on the monitor. This allows the surgeon to monitor and track the adjustments of the repair apparatus 5.

Peripheral illumination passageways 312 and 313 are provided for the passage of illuminating means 330 for illuminating the abdominal aorta for viewing by the optical viewing means 320. In a preferred embodiment, the illuminating means 330 is a fiber optic system including a fiber optic bundle. It, however, will be apparent to those skilled in the art that various modifications and variations can be made in the construction and configuration of the present invention without departing from the scope or spirit of the invention. For example, the illuminating means 330 mentioned above, may be any system that is sized for use in surgical applications and capable of illumination within the aorta. Although a pair of passageways are illustrated, it is contemplated that a single illumination passageway will provide sufficient illumination. Additionally, more than two passageways may also be provided.

Peripheral fluid inflow passageway 314 and peripheral fluid outflow passageway 315 are provided for the passage of fluid lens media to and from the visualization tip 340. The peripheral fluid inflow passageway 314 supplies a stream of optically clear fluid lens media from the visualization tip 340 in the area in front of the optical viewing means 320. A control means, not shown, may be incorporated into passageway 314 to control the flow volume and velocity of the fluid lens media to the visualization tip 340. The control means may be a valve or other suitable flow control devices. The control means controls the optically clear fluid lens media such that blood within the aortic cavity and the fluid lens media are pressure balanced. As a result, blood that is typically within the aorta is temporarily diverted away by the fluid lens media to a point adjacent the area of the wall 2 to be viewed by the optical viewing means 320. The infusion of fluid lens media will dilute blood to an appropriate transparency in the immediate surgical site to exclude blood between the visualization tip 340 and the surgical site on the wall 2. This permits the surgeon to clearly view the wall 2 through the optical viewing means 320. In a preferred embodiment, the fluid lens is a transparent fluid to permit viewing of the wall 2. The fluid lens media may be a saline solution. It is preferred that the solution be used for a single application (i.e., it is not reused). Other media, such as $CO_2$ gas and GreenX liquid fluorocarbon are contemplated to be within the scope of the present invention. The peripheral fluid outflow passageway 315 acts as a return duct for the fluid lens media within the aorta. Alternatively, the fluid lens media may then be filtered using an appropriate filtering means and recirculated using a pumping means through the peripheral fluid inflow passageway 314.

In a preferred embodiment, it is contemplated that the visualization apparatus 6 be used in combination with the introducer sheath devices 900, described below. The introducer sheath devices 900 and in particular the positioning assembies 920 permit the isolation of a portion of the vessel during the repair procedure. Specifically, the positioning assemblies 920 within the common iliacs and femoral artery permit the control of blood within the vessel. With this arrangement, it is then possible to more readily divert blood away from a viewing area with the flow of fluid lens media from the fluid inflow passageway 314.

A visualization tip 340 is securely mounted to the end of housing 300 in a fluid tight manner. The tip 340 may be snap fitted or permanently mounted to the housing 300. It, however, will be apparent to those skilled in the art that various modifications and variations can be made in the construction and configuration of the present invention without departing from the scope or spirit of the invention. For example, the visualization tip 340 mentioned above, may be secured to the housing 300 by means other than the above described snap and permanent fittings. The visualization tip 340 may be formed by injection molding or other suitable manufacturing methods in silicone or similar polymer.

The visualization tip 340 comprises apertures 341, 342, 343, 344, and 345 that correspond to passageways 311, 312, 313, 314, and 315, respectively. Aperture 341 contains a lens positioned therein to facilitate viewing of the wall 2 with the optical viewing means 320. Apertures 342 and 343 may include windows therein whereby light from the illuminating means 330 passes through the windows to illuminate the wall 2, although it is not necessary. Apertures 344 and 345 act as gates for the peripheral fluid inflow passageway 314 and peripheral fluid outflow passageway 315. The aperture 344 may be inwardly tapered, such that the inside diameter of the aperture adjacent the inflow passageway 314 is greater than the diameter on the outer surface of the tip 340 to concentrate the stream of fluid lens media from the fluid inflow passageway 314. The aperture 345 may be outwardly tapered, such that the inside diameter of the aperture adjacent the inflow passageway 315 is less than the diameter on the outer surface of the tip 340. It is contemplated that the tip 340 is optional.

Penetration Apparatus

Figure 16:
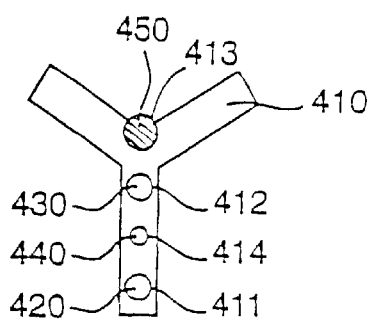
FIG. 16 is an end view of the penetration device according to an embodiment of the present invention.
Figure 17:
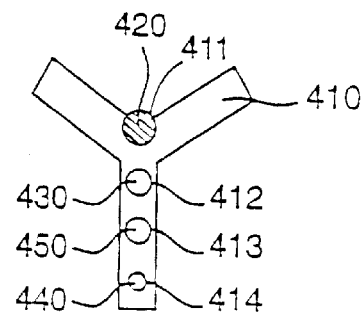
FIG. 17 is an end view of the penetration device according to another embodiment of the present invention.

A penetration apparatus 7 will now be described in connection with FIGS. 15–20. The penetration apparatus 7 may be inserted within the repair apparatus 5, 500, 5000, as shown in FIGS. 15A–D, for fastening a repair graft to the vessel wall 2. The penetration apparatus 7 comprises several components for fastening a repair graft including penetration means 420, secondary penetration means 430, tracking means 440 and insertion means 450. The penetration apparatus 7 comprises housing 410 for housing the penetration means 420, secondary penetration means 430, tracking means 440 and insertion means 450. In a preferred embodiment, the housing 410 has a thin walled tri-limbed profile, as shown in FIGS. 15C, 16, and 17. In a preferred embodiment for increased flexibility, the housing 410 is positioned within the repair apparatus 5 such that two of the three limbs of the housing 410 are spaced from the side of housing 200 containing the guide wire 160. It, however, will be apparent to those skilled in the art that various modifications and variations can be made in the construction and configuration of the present invention without departing from the scope or spirit of the invention. For example, the housing 410 mentioned above, may have more than three limbs. Alternatively, the housing 410 may be cylindrical having a plurality of inwardly projecting limbs. An alternative configuration for housing 4100 is depicted in FIGS. 15B and 15D. The housing 4100 comprises a central passageway 4110 containing penetration means 420. Additional passageways 4210 and 4130 are provided for other components such as secondary penetration means, tracking means and insertion means.

The housing 410 is preferably formed from an extrusion of silicone, Teflon®, or polymer having similar properties. Housing 410 comprises a plurality of passageways 411, 412, 413, and 414, formed therein as shown in FIG. 16. An alternative arrangement is shown in FIG. 17. The passageways 411, 412, 413, and 414 extend along the entire length of the housing means 410. Primary passageway 411 is provided for the passage of the penetration means 420. The penetration means 420 is provided to create a treatment specific hole in the wall 2 of the abdominal aorta for securing the graft thereto with a suitable fastener device, described below. The penetration means 420 penetrates the potentially calcified vessel wall 2 to securely fasten the repair graft to the wall 2. The penetration means 420 may be either a laser penetrating device or a piezoelectric penetrating device. It, however, is contemplated by the inventors of the present invention that other penetration means including but not limited to $CO_2$ penetration, micro electromechanical systems, and intraluminal suturing are considered to be within the scope of the present invention. The laser penetrating device 420 preferably is an IR fiber optic based system using laser energy to create treatment specific holes in the aorta wall 2. The fused silica/quartz fibers that are utilized are in the 200–600 micron size range. Suitable lasers comprise but are not limited to an acousto optical laser having a wavelength of about 1.35 $\mu$m, and a Holmium-Yag laser having a wavelength of about 2.1 $\mu$m. The selected wavelength allows transition of laser energy through the fiber in the passageway 411. The laser fiber will be in direct contact with the surgical site such that the fiber projects from the end of the housing 410. It is contemplated that a single, or tri-pronged hole pattern will be created using penetration means 420 and secondary penetration means 430.

The piezoelectric penetrating device preferably is a catheter based system, which utilizes acoustic vibrations to create treatment specific suture holes to aid in graft/tissue attachment. The piezoelectric penetrating device applies an "acoustic wave" effect to create holes in the graft and vessel wall. In this variation, the passageway 411 preferably contains a super elastic titanium catheter, in rod or tube form, which enables transmittance of energy through the sometimes tortuous vessels to the surgical site. The catheter will be in direct contact with the surgical site such that the catheter projects from the end of the housing 410 into the formed treatment specific hole. The secondary penetration means 430 creates one or more temporary hole(s). The piezoelectronic device preferably operates at a frequency of 20 KHz. Other frequencys, both higher and lower, are contemplated to be within the scope of the present invention. The primary penetration means 420 is coaxial with the fastener devices such that the fastener devices may be inserted through the treatment specific hole created by the primary penetration means 420.

Secondary passageway 412 is provided for the passage of the secondary penetration means 430. The secondary penetration means 430 is also provided to create one or more temporary holes in the vessel wall 2, in a manner similar to the primary penetration means 420. Similarly, the secondary penetration means 430 may be either a laser penetrating device or a piezoelectric penetrating device, as described above in connection with the penetration means 420. The secondary penetration means 430 serves to anchor and orient the penetration apparatus 7 while a fastener is inserted within the treatment specific hole formed by the primary penetration means 420. After the secondary penetration means 430 is removed, the temporary holes will seal with blood that will coagulate.

Passageway 413 is provided within the housing 410 for passage of the insertion means 450, described below. Passageway 414 is provided within the housing means 410 for passage of the tracking means 440. In a preferred embodiment, the tracking means 440 is a radiopaque marker, which is utilized for the purpose of identifying the location of the penetration apparatus 7 within the image on the monitor. It, however, will be apparent to those skilled in the art that various modifications and variations can be made in the construction and configuration of the present invention without departing from the scope or spirit of the invention. For example, the tracking means 440 mentioned above, may be a tip-tracking device or a fiber optic aiming beam.

Figure 18:
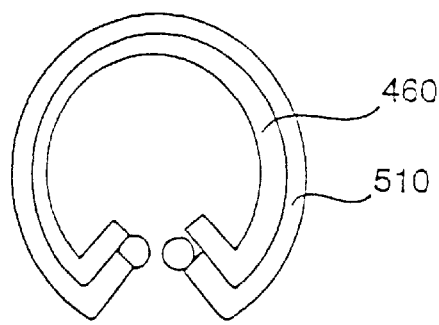
FIG. 18 is an end view of the fastener cartridge according to the embodiment of FIG. 15

Insertion means 450 for securing the repair graft to the wall 2 during repair of the aneurysm will be described in connection with FIG. 19. The insertion means 450 preferably comprises a mechanism that drives an individual fastener from a fastener cartridge 460, shown in FIGS. 15 and 18, into and through the treatment specific holes created by the penetration means 420 in the repair graft and wall 2. The fastener cartridge 460 is capable of holding a plurality of fasteners such that more than one fastener may be sequentially displaced from the cartridge 460 to secure the repair graft to the abdominal aorta wall 2. Fastener cartridge 460 is preferably detachably connected to housing 410. The fastener cartridge 460 is a hollow housing, as shown in FIG. 18, preferably formed of injection molding HDPE or Liquid Crystal, manufactured by the RTP Co. of MN. The penetration means 420 and 430, the tracking means 440 and the insertion means 450 are appropriately accommodated within the interior of the cartridge structure 460. The cartridge 460 is positioned about the housing 410.

Figure 19:
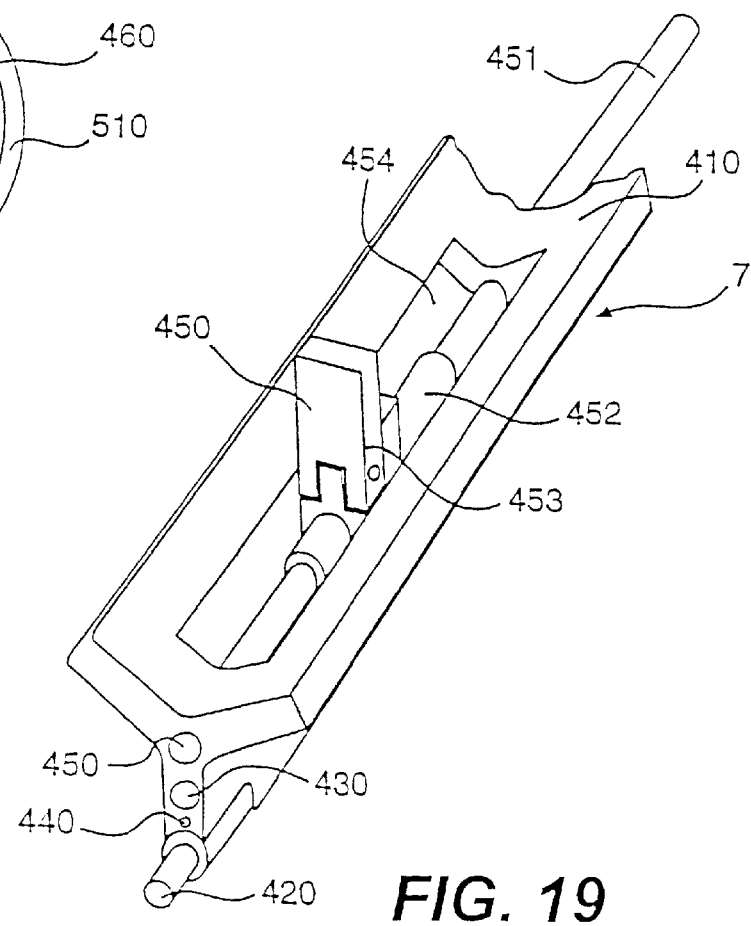
FIG. 19 is a perspective view of an advancing mechanism of a penetration device according to an embodiment of the present invention.

The insertion means 450 illustrated in FIG. 19 comprises a driving means 451 for driving the fastener devices to secure the repair graft to the vessel wall 2. A gear 452 and fastener advancing means 453 are positioned within an opening 454 in housing 410. In a preferred embodiment, the gear 452 is a worm gear. However, other suitable gear assemblies are contemplated to be within the scope of the present invention. The gear 452 is connected to the driving means 451. The fastener advancing means 453 interacts with the gear 452 to advance a fastener device to secure the repair graft to the vessel wall 2. In a preferred embodiment, the fastener advancing means 453 is an internally geared drive plate assembly. The drive plate assembly may be capable of limited angular adjustment. Operation of the insertion means 450 is controlled by a control device, not shown, such that upon actuation by the control device, the fastener advancing means 453 is advanced to eject a fastener device from fastener cartridge 460. Alternatively, the insertion means 450 may be hand operated. The insertion means 450 is used, for example, in the embodiment illustrated in FIG. 15C.

Figure 20:
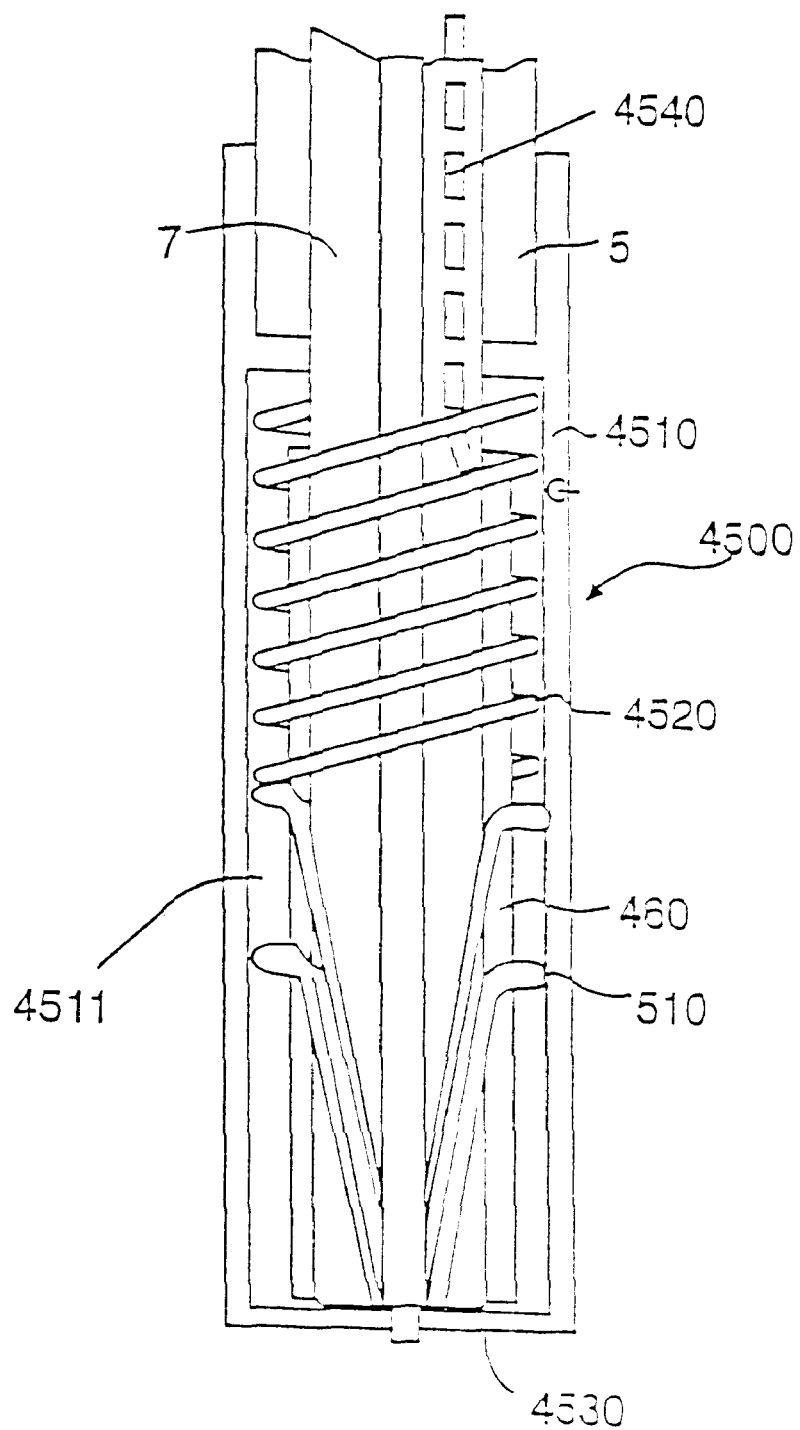
FIG. 20 is a schematic view of another advancing mechanism of a penetration device and fastener cartridge according to another embodiment of the present invention.

Another embodiment of the insertion means 4500 is illustrated in FIG. 20. An insertion cartridge 4510 is secured to the distal end of the repair apparatus 5. The insertion cartridge 4510 may be snap fitted to the housing 200. The insertion cartridge 4510 comprises a cavity 4511. A spring means 4520 is positioned within the cavity 4511. A fastener cartridge 460 is also located within the cavity 4511. An opening 4530 is located at one end of the insertion housing 4510. The housing 410 of the penetration apparatus 7 normally prevents the spring means 4520 from ejecting a fastener device through the opening 4530. The insertion means 4500 comprises retraction means 4540 which retracts the housing 410 away from the opening 4530 which permits the fastener to be ejected into the treatment specific hole created by the primary penetration means 420. The retraction means 4540 may be a cable that acts to retract the housing 410 away from opening 4530. The release of the retraction means 4540 causes the housing 410 to return to the position adjacent the opening 4530 to prevent the discharge of a subsequent fastener device.

Intravascular UltraSound (IVUS) Repair System

Reference will now be made in detail to preferred embodiments of an apparatus according to the present invention for facilitating the repair of abdominal aortic aneurysms using above described repair grafts. An example of an intravascular ultrasound based system is depicted in FIGS. 21–24.

Figure 23:
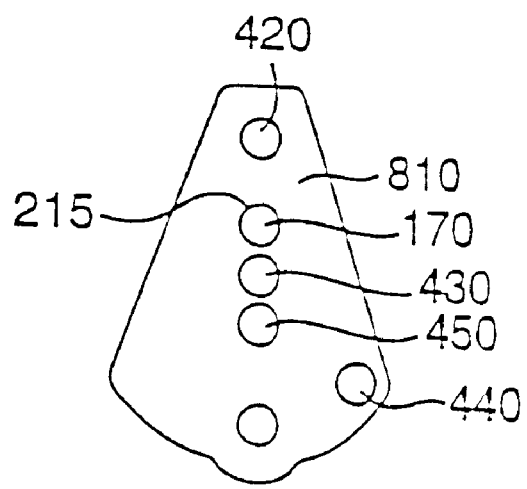
FIG. 23 is a cross sectional view of a housing according to an embodiment of the present invention.

The repair apparatus 50 comprises housing 800. The housing 800 comprises a major guide wire portion 810, a cross-section of which is shown in FIG. 23, a spacer portion 820, and a minor guide wire portion 830.

Positioned within the housing 800 is an apparatus guide means 214 for guiding the repair apparatus 50 within the vessel 1 during use. The guide means 214 preferably is a passageway or lumen extending the length of the housing 800 through major guide wire portion 810, the spacer portion 820, and the minor guide wire portion 830. A guiding means 160 cooperates with guide means 214 to guide the apparatus 50 during use. The guiding means 160 is preferably a guide wire which is capable of extending from the femoral artery to the axillary artery. In a preferred embodiment, the guide wire 160 is a filament (e.g., stainless steel, titanium or Kevlar® cable). It, however, will be apparent to those skilled in the art that various other materials having similar properties of physical integrity, high strength, flexibility, and minimal thermal expansion may be used to form the guide wire 160.

Housing 800 also comprises an apparatus manipulation means 215 to aid in manipulating and orienting the penetration apparatus 700 within the vessel 1 during the repair operation. The manipulation means 215 preferably comprises at least one passageway extending within the housing 810. The manipulation means 215 mates with complimentary passageways formed in housing 710. A manipulating means 170 cooperates with manipulation means 215 to guide the apparatus 50 during use. The manipulating means 170 is preferably comprises at least one guide wire that is capable of extending from outside the patient through the housings 810 and 710. The guide wire 170 extends through the manipulating means 215. In a preferred embodiment, the guide wire 170 is a super elastic metal filament. It, however, will be apparent to those skilled in the art that various other materials having similar properties of physical integrity, high strength and flexibility may be used to form the guide wire 170.

Operation of the manipulating means 170 results in the articulation of an end portion of the housing 710. The guide wire 170 maintains the housing 710 in an articulated position, as shown in FIG. 21, during the repair operation.

Figure 24:
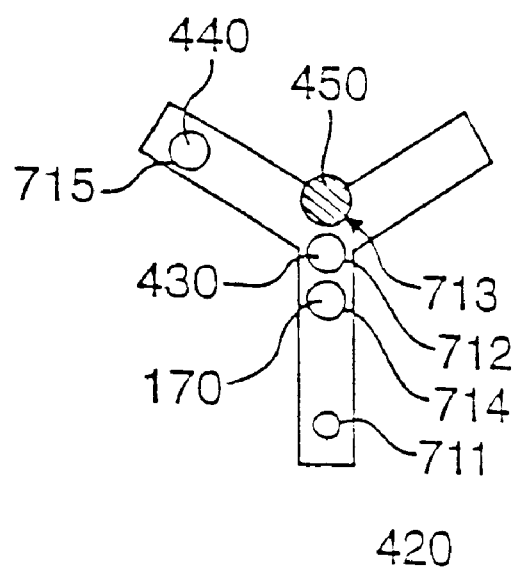
FIG. 24 is an end view of a penetration device depicted in FIG. 21.

The penetration apparatus 700 will now be described in connection with FIGS. 21–24. The penetration apparatus 700 comprises several components for fastening a repair graft including penetration means 420, secondary penetration means 430, tracking means 440, and insertion means 450. The penetration apparatus 700 comprises housing 710 for housing the penetration means 420, secondary penetration means 430, and insertion means 450. In a preferred embodiment, the housing 410 has a thin walled tri-limbed profile, as shown in FIGS. 21, 22 and 24. It, however, will be apparent to those skilled in the art that various modifications and variations can be made in the construction and configuration of the present invention without departing from the scope or spirit of the invention.

The housing 710 is preferably formed from an extrusion of silicone, Teflon®, or polymer having similar properties. Housing 710 comprises a plurality of passageways 711, 712, 713, 714, and 715 formed therein as shown in FIG. 24. The passageways 711, 712, 713, 714 and 715 extend along the entire length of the housing 710. Primary passageway 711 is provided for the passage of the penetration means 420. The penetration means 420 is provided to create an treatment specific hole in the wall 2 of the abdominal aorta for securing the graft thereto with a suitable fastener device. The penetration means 420 penetrates the calcified portions of the wall 2 to securely fasten the repair graft to the wall 2 in the same manner as described above in connection with the endoscopic based system. The penetration means 420 may be either a laser penetrating device or a piezoelectric penetrating device.

Secondary passageway 712 is provided for the passage of the secondary penetration means 430. The secondary penetration means 430 is also provided to create one or more openings in the vessel wall 2, in a manner similar to the primary penetration means 420, as described above.

Passageway 713 is provided within the housing 710 for passage of the insertion means 450. Passageway 714 is provided within the housing 710 for passage of the guide wire 170. Passageway 715 is provided for tracking means 440. The insertion means 450 preferably comprises a mechanism that drives an individual fastener from a fastener cartridge 470, shown in FIGS. 21 and 22, into and through the treatment specific holes created by the penetration means 420 in the repair graft and wall 2. The fastener cartridge 470 is capable of holding a procedure specific quantity of fasteners such that more than one fastener device may be sequentially displaced from the cartridge 470 to secure the repair graft to the wall 2. Fastener cartridge 470 is preferably detachably assembled to housing 710. The fastener cartridge 470 has a hollow housing 471, as shown in FIG. 21. The penetration means 420 and 430, and the placement/fastener means 450 are appropriately accommodated within the interior of the cartridge structure 460. The cartridge structure 470 and associated fastener device are complimentary with the spacer portion 820 of the housing 800 such that the penetration apparatus 700 has a flush profile, as shown in FIG. 22.

A visualization apparatus 600 for viewing the abdominal aorta to repair the aneurysm is positioned within housing 800 adjacent the minor guide wire portion 830. The visualization apparatus 600 is an intravascular ultrasound (IVUS) based system produced, for example, by Endosonics of Rancho Cordova, Calif., that comprises a housing 601 for housing radial scanning components. The housing 601 may comprise a scanning window 602, however, it is not essential for the effective operation of the visualization apparatus 600. The visualization apparatus comprises scanning catheter positioned within the housing 601 such that it scans the area of the abdominal aorta. The housing 601 is an extrusion of silicon, Teflon® or polymer or other material having similar properties. The scanning catheter extends through the minor guide wire portion 830 of housing 800. The scanning catheter creates an image of the repair that can be viewed on an external monitor, not shown.

The housing 800 also comprise transition portions 801 and 802 located on opposite ends of the penetration apparatus 700 to provide the repair apparatus 50 with a smooth profile, as shown in FIG. 22. This improves the movement of the repair apparatus 50 within the vessel 1 and adjacent arteries.

Fasteners

Reference will now be made in detail to preferred embodiments of a fastener device, as depicted in FIGS. 25–32, according to the present invention for securing the attachment device 20 to the distal end of the vessel 1. Although the fastener devices are described in connection with the repair of an aneurysm in a vessel, the use of the fastener devices in other surgical procedures as a replacement for sutures is contemplated to be within the scope of the present invention.

Figure 25:
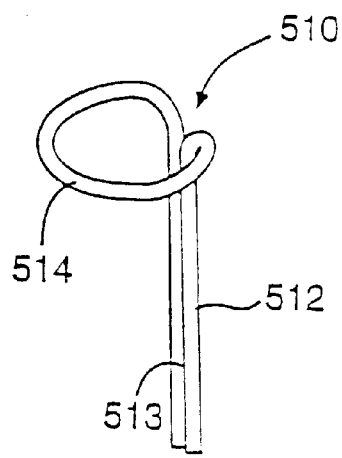
FIGS. 25 and 26 are perspective views of a wire fastener for securing the cuff detail of a surgical cuff to a vessel wall according to an embodiment of the present invention.
Figure 26:
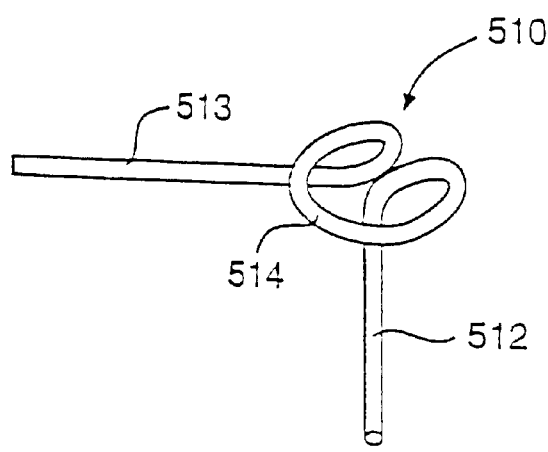

FIGS. 25 and 26 depict a fastener 510 according to an embodiment of the present invention. The fastener 510 comprises a pair of normally splayed fastening legs 512 and 513. The fastener 510 also comprises an anchoring portion 514. The fastener 510 is preferably formed from a wire-like material. The anchoring portion 514 may be formed from a coil of the wire-like material. The legs 512 and 513 are temporarily reoriented, as shown in FIG. 25, for storage on a fastener cartridge 460 and for enabling the attachment of the attachment device 20 to the wall 2. As the legs 512 and 513 are inserted through the attachment device 20 and the wall 2, the legs 512 and 513 return to a normal, as manufactured, splayed position, as shown in FIG. 26. When the fastener 510 is in a fastened position within the vessel, the anchoring portion 514 is positioned on one side of the attachment device 20 and wall 2 (intima/graft) adjacent the attachment device 20. The splayed legs 512 and 513 are positioned on the opposite side of the attachment device 20 and wall 2 (adventia) adjacent the wall 2. The anchoring portion 514 and splayed legs 512 and 513 apply compressive forces to the wall 2 and the attachment device 20 to securely fastening the attachment device 20 to the vessel 1.

The fastener 510 is preferably formed from a stainless steel, such that the legs 512 and 513 return to the splayed position to secure the attachment device 20 to the wall 2. It, however, will be apparent to those skilled in the art that various modifications and variations can be made in the construction and configuration of the present invention without departing from the scope or spirit of the invention. For example, the fastener 510 may be formed from other suitable materials including but not limited to superelastic titanium, or other procedure/performance-appropriate materials having similar properties including, but not limited to biocompatability, elasticity, and flexural strength. Thus, it is intended that the present invention cover the modifications and variations of the invention, provided they fall within the scope of the appended claims and their equivalents.

Figure 27:
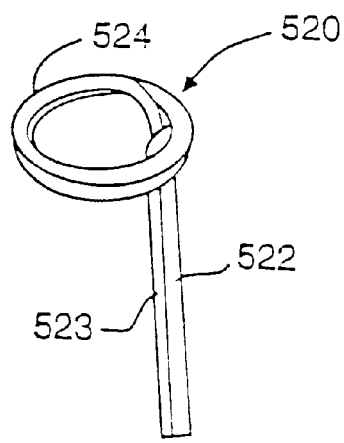
FIGS. 27 and 28 are perspective views of a wire fastener according to another embodiment of the present invention for securing the cuff detail of a surgical cuff to a vessel wall.
Figure 28:
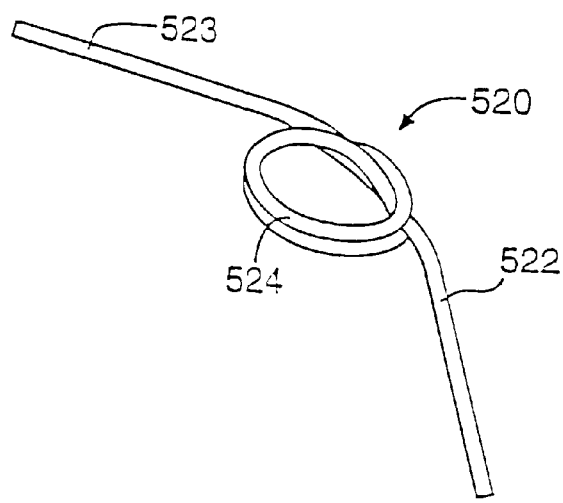

FIGS. 27 and 28 depict a fastener 520 according to an another embodiment of the present invention. The fastener 520 comprises a pair of normally splayed fastening legs 522 and 523. The fastener 520 also comprises an anchoring portion 524. The fastener 520 is also preferably formed from a wire-like material. The anchoring portion 524 may be formed from at least one coil of the wire-like material (i.e., a wound portion). The legs 522 and 523 are temporarily compressed, as shown in FIG. 27, for storage in a fastener cartridge 460 and for facilitating the attachment of the attachment device 20 to the wall 2. Similar to the embodiment described above in connection with FIGS. 25 and 26, as the legs 522 and 523 are inserted through the attachment device 20 and the wall 2, the legs 522 and 523 return to a normally splayed position, as shown in FIG. 27. When the fastener 520 is in a fastened position within the vessel, the anchoring portion 524 is positioned on one side of the attachment device 20 and wall 2 adjacent tile attachment device 20. The splayed legs 522 and 523 are positioned on another side of the attachment device 20 and wall 2 adjacent the wall 2. The anchoring portion 524 and splayed legs 522 and 523 apply compressive forces to the wall 2 and the attachment device 20 to securely fastening the attachment device 20 to the vessel 1.

Figure 33:
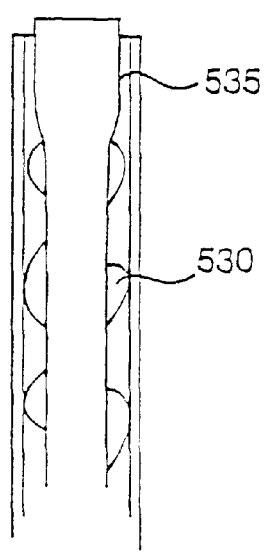
FIG. 33 is a schematic view of an embodiment of the penetration device according to the present invention having fasteners, as shown in FIGS. 31, 32a, 32b and 32c stored thereon.
Figure 34:
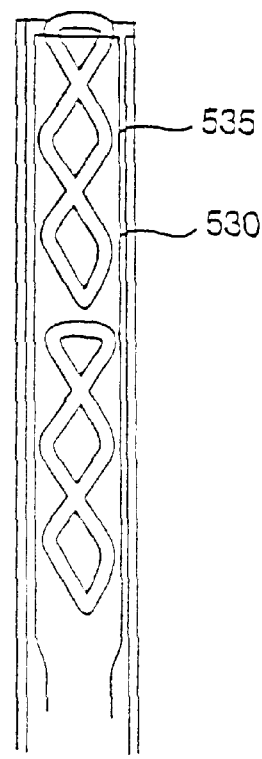
FIG. 34 is a schematic view of an another embodiment of the penetration device according to the present invention having fasteners, as shown in FIGS. 31, 32a, 32b and 32c stored therein.
Figure 35:
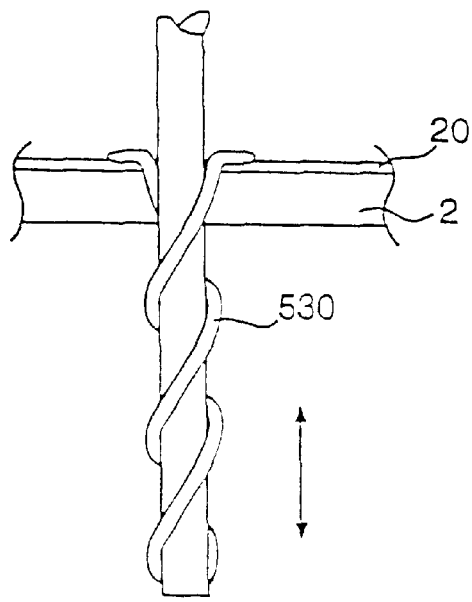
FIGS. 35 and 36 are perspective views illustrating the fastener attachment of the cuff detail to the vessel wall using a fastener as shown in FIGS. 29 and 30 according to an embodiment of the present invention.
Figure 36:
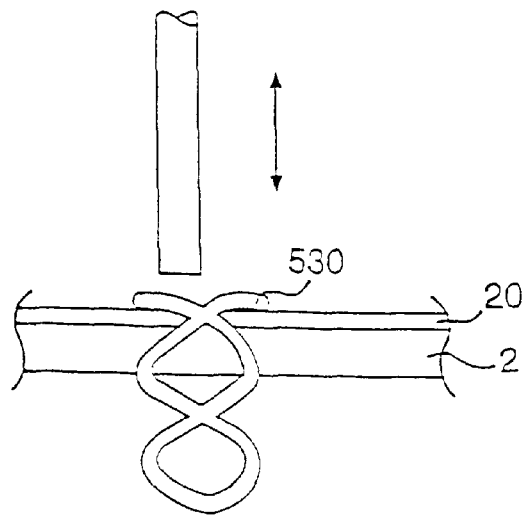
Figure 37:
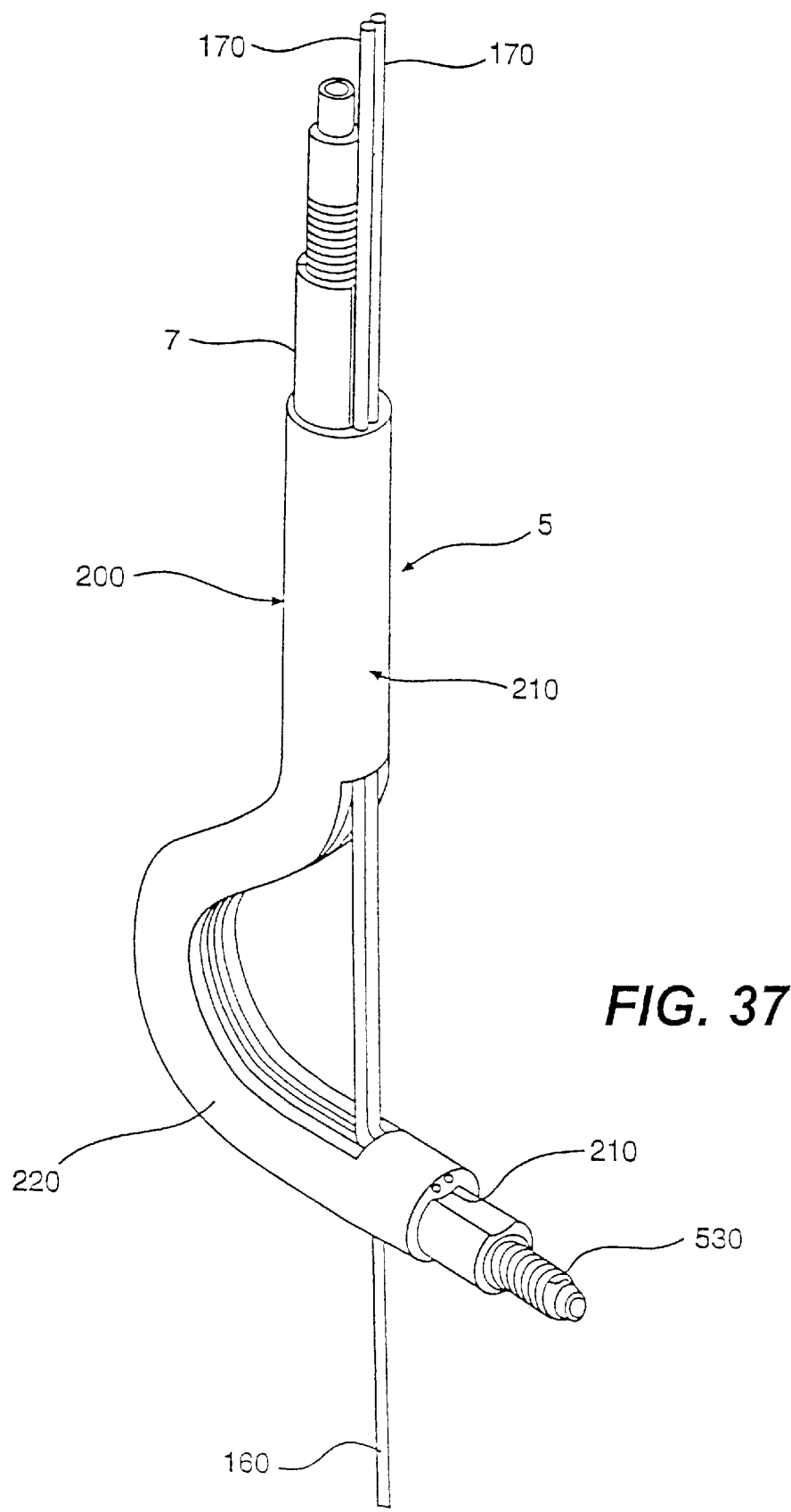
FIG. 37 is a perspective view of another embodiment of an IntraVascular Endoscopy (IVE) based repair system according to an another embodiment of the present invention.

FIGS. 29 and 30 depict a fastener 530 according to another embodiment of the present invention. Fastener 530 is a spring type fastener, which may comprise a coil spring. The fastener 530 is also formed from a wire-like material. The fastener 530 comprises a plurality of coils, as shown in FIG. 29. The end portions 531 and 532 of the wire-like material are preferably located on the same end of the fastener 530, as shown in FIGS. 29, 30, and 34–36. Unlike fastener 510 and 520, the fastener 530 is temporarily elongated for storage in the fastener cartridge 535, as shown in FIGS. 33, 34, and 37. As the fastener 530 is inserted through the attachment device 20 and wall 2 using the insertion means 450 on the penetration device 7, as shown in FIG. 35, the fastener 530 remains in an elongated position until the insertion means 450 is removed from the treatment specific hole 3 created in the wall 2 of the vessel 1 and the attachment device 20 formed by the penetration apparatus 7. The fastener 530 then assumes a collapsed position, as shown in FIG. 30. When the fastener 530 is in a fastened position within the vessel 1, the end portions 531 and 532 are positioned on one side of the attachment device 20 and wall 2 adjacent the attachment device 20, as shown in FIG. 36. The remaining portion of the fastener 530 is positioned on another side of the attachment device 20 and wall 2 adjacent the wall 2. The fastener 530 applies compressive forces to the wall 2 and the attachment device 20 to securely fastening the attachment device 20 to the vessel 1. Fastener 530 may be formed from a suitable, stainless steel, a superelastic alloy, or any other procedure/performance-appropriate materials.

Figure 32B:
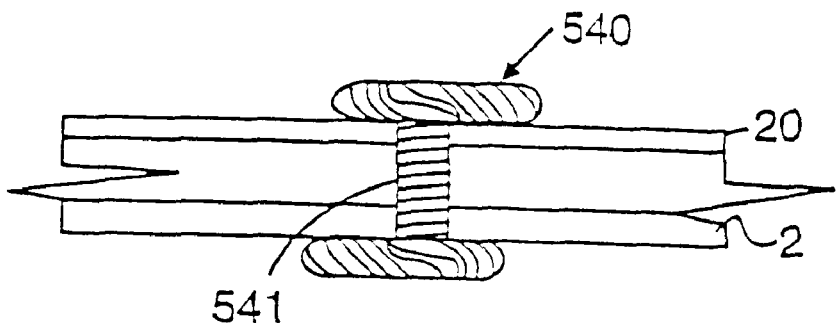
Figure 32C:
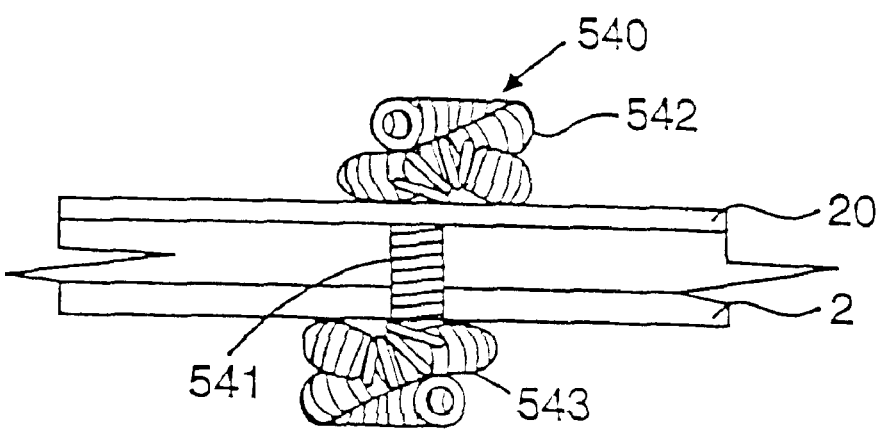
Figure 32D:
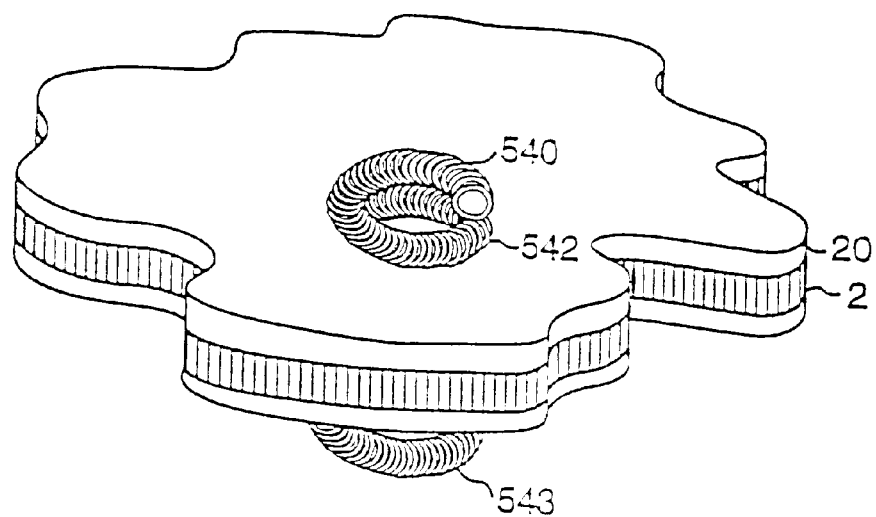
Figure 32E:
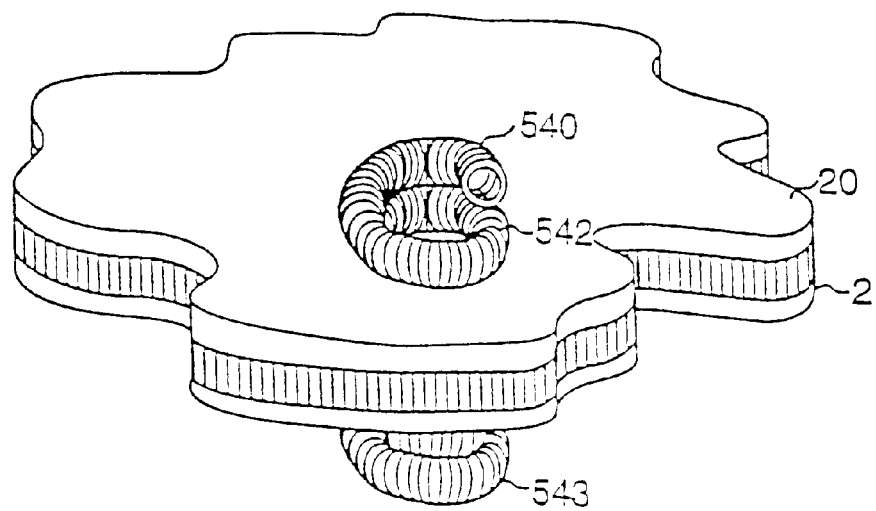

FIGS. 31, 32a, 32b, and 32c depict a fastener 540 according to another embodiment of the present invention. Fastener 540 is a coil spring type fastener. Fastener 540 comprises a mid-section 541, and semi-knotted end portions 542 and 543. The fastener 540 is also formed from a coil spring using materials, as described above. The fastener 540 is substantially linear, as shown in FIG. 31, for storage in a fastener cartridge, not shown. As the fastener 540 is inserted through the attachment device 20 and wall 2, the fastener 540 returns to its normally coiled position, as shown in FIG. 32a. The fastener 540 applies compressive forces to the wall 2 and the attachment device 20 to securely fastening the attachment device 20 to the vessel 1 such that one semi-knotted end portion 542 is positioned adjacent the attachment device 20 and the other semi-knotted end portion 543 is positioned adjacent the wall 2 of the vessel 1, as shown in FIGS. 32b and 32c. FIG. 32b depicts an axially wound fastener 540. FIG. 32d depicts the fastener 540 of FIG. 32b secured to the wall 2. FIG. 32c depicts a radially wound fasteners 540. FIG. 32e depicts the fastener 540 of FIG. 32c secured to the wall 2.

It, however, will be apparent to those skilled in the art that various modifications and variations can be made in the construction and configuration of the present invention without departing from the scope or spirit of the invention. For example, the fastening means mentioned above, may be pop-rivet fasteners, screw-type fasteners, rapid hardening plastic extrudates, and other suitable fasteners are contemplated to be within the scope of the present invention. Thus, it is intended that the present invention cover the modifications and variations of the invention, provided they fall within the scope of the appended claims and their equivalents.

Introducer Sheath Devices

Figures 38, 39:
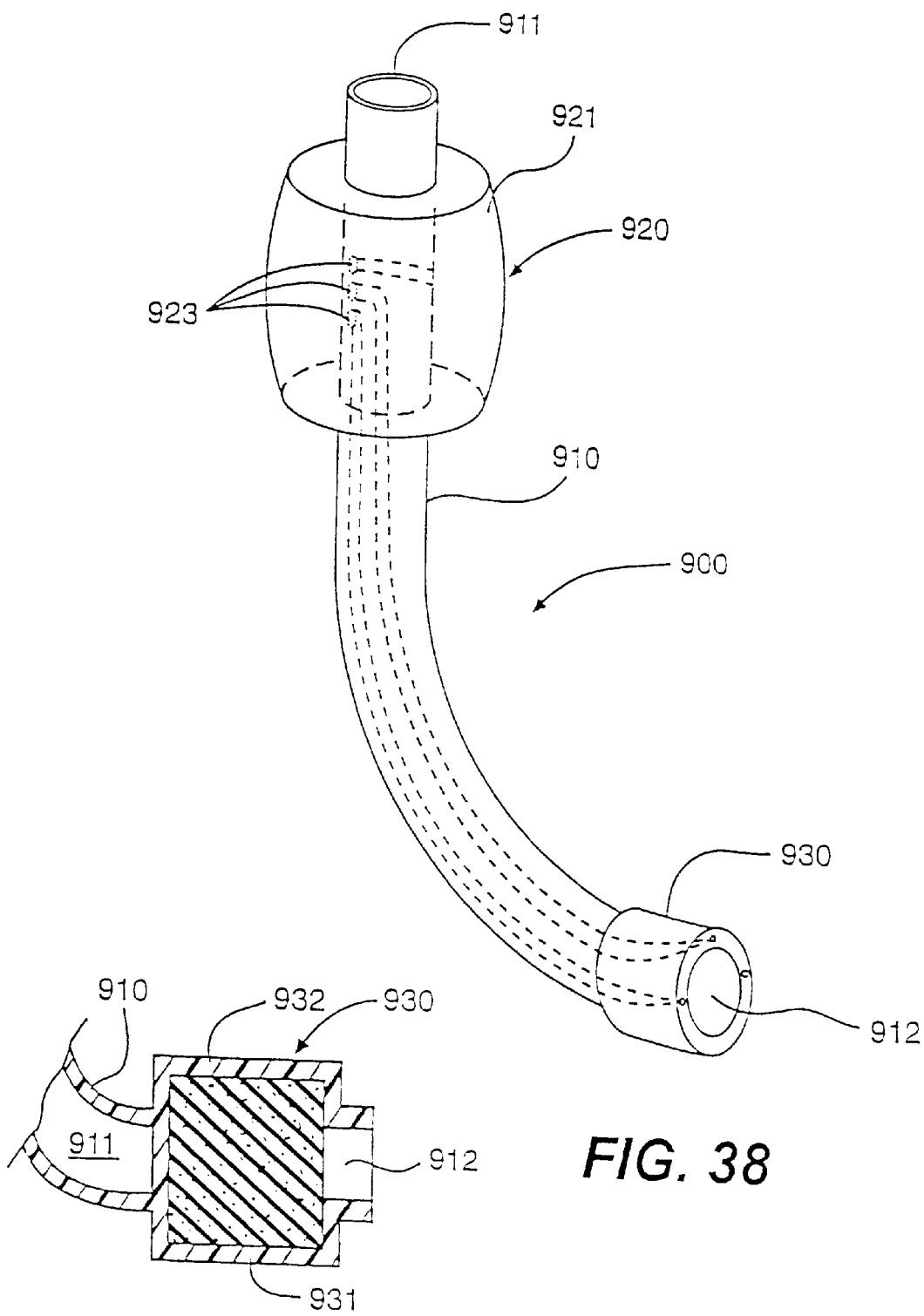
FIG. 38 is a perspective view on an introducer sheath device according to the present invention; and, FIG. 39 is a cross sectional view of a seal assembly for the introducer sheath device according to an embodiment of the present invention.

Reference will now be made to a preferred embodiment of an introducer sheath device according to the present invention of use in the repair of abdominal aneurysms, an example of which is illustrated in FIGS. 38 and 39. The introducer sheath devices create a protective passageway through the vessel through which the graft and repair devices are inserted. The introducer sheath devices protect the arteries from damage that may occur when the repair apparatus and other device are passed through the tortuous artery passageways during a surgical procedure.

Existing methods for repairing aneurysms utilize introducer sheath devices only in the femoral and common iliac arteries. Typically, guide wires extend from a femoral arteriotomy to an occlusion balloon placed within the proximal neck of the aorta at a point cephalad with respect to the abdominal aorta. Typically, others have gained access to the abdominal aorta via a femoral or common iliac arteriotomy into which is inserted an introducer sheath device of between 18–28 Fr. diameter. The size of these devices may cause damage to the vessels through which they pass.

By contrast, the inventors of the present invention contemplate the use of more than one unique introducer sheath device 900, as shown in FIG. 33. The sheaths 900 are introduced over a femoral/axillary guide wire. One introducer sheath device 900 extends from either an axillary incision or a brachial incision to the proximal neck of the vessel 1. Another introducer sheath device 900 extends from a femoral incision to the distal neck of the vessel or common iliac/distal aorta transition. The introducer sheath devices according to the present invention that extend through the axillary vessel and through the femoral artery have similar constructions. However, the introducer sheath device that extends through the axillary artery has a smaller size in the range between 9–12 Fr. and is able to navigate the arteriotomy/distal aorta passageway without problem. The smaller size will permit access to the aorta via either the left brachial or axillary artery, both of which are significantly smaller than the femoral or common iliac arteries. This procedure, previously, beyond consideration, may now significantly benefit these vascular surgeries.

Each introducer sheath device 900 comprises a housing 910 having a hollow interior 911 that permits the passage of the tube graft and other repair apparatus through the introducer sheath device to the vessel 1. The repair apparatus are introduced through the an opening 912 in the end portion of the housing 910. In a preferred embodiment, the housing 910 is a thin walled co-extrusion having an outer surface formed, for example, from silicon and an inner surface formed, for example, from Teflon®. Alternatively, the housing 910 may be formed of a suitable polymer having similar properties.

The introducer sheath device 900, also, comprises positioning assembly 920 for maintaining the sheath 900 in proper orientation within the vessel. In a preferred embodiment, the positioning assembly 920 comprises an inflatable cuff 921 located at one end of housing 910. The positioning assembly 920 further comprises an inflation device for inflating the cuff 921. The inflation device in a preferred embodiment comprises a plurality of passageways 923 formed within the wall of housing 910. A suitable fluid, such as saline, is supplied from an external source through the passageways 923 to fill the cuff 921. The passageways 923 terminate at inflatable cuff 921, as shown in FIG. 38.

Prior introducer sheath devices have not been able to control the loss of significant amounts of blood through the open end of the introducer sheath device that is positioned outside of the body. Others have attempted to prevent this blood loss through the use of complex clamping systems. The present invention provide a unique seal arrangement to prevent significant blood loss. A seal 930 located at one end of the housing 910 adjacent opening 912 will prevent significant blood loss. The seal 930 comprises an expanded housing assembly 931. A self-sealing gel-like material 932 is located within the expanded housing assembly 931. The material 932 permits the insertion of the repair apparatus through the material 932, which forms a seal around the repair apparatus. As a the repair apparatus is removed from the introducer sheath device 900, the material 932 forms a seal behind the repair apparatus as it is removed through opening 912.

It, however, will be apparent to those skilled in the art that various modifications and variations can be made in the construction and configuration of the present invention without departing from the scope or spirit of the invention. It is intended that the present invention cover the modifications and variations of the invention, provided they fall within the scope of the appended claims and their equivalents.

Method of Repairing an Aneurysm

Reference will now be made in detail to a preferred embodiment of the method of repairing an aneurysm utilizing the above described components according to the present invention.

IntraVascular Endoscopy (IVE) Based Repair Method

The IntraVascular Endoscopy (IVE) based repair method will be described in connection with the use of a proximal graft assembly 10 and distal graft assembly 20. Introducer sheath devices 900 are placed by femoral arteriotomy in both common iliacs under radiological guidance such that the positioning assembly 920 is positioned at the common iliac/aortic bifurcation transition. A guide wire is fed from one femoral incision to the other, also under guidance. A distal graft assembly 20 is fed over the guide wire until the attachment cuff 21 appears directly above the carina at the bifurcation, as shown in FIG. 1A.

A second guide wire 160 is now fed under radiological guidance between one femoral incision and the left axillary incision. Another introducer sheath device 900 is fed from the axillary until the positioning assembly 920 reaches the infrarenal aorta at which time it is inflated. The repair apparatus 5 is then fed through the introducer sheath device 900 over guide wire 160 from either the femoral or axillary access to the midpoint of the aortic aneurysm. The visualization apparatus 6 is then fed through the hollow interior 211 of housing 200 to the area of the wall 2 to which the attachment cuff 22 is to be attached. The guide wires 170 are then manipulated to adjust the orientation of the visualization apparatus 6 to permit viewing of the wall 2 as described above, such that an image appears on the monitor. An image of the wall 2 appears on the monitor. The visualization apparatus 6 is then removed and the penetration apparatus 7 is then inserted through the hollow interior 211. The guide wires 170, as described above, permit the penetration apparatus to be positioned in the same position as the visualization apparatus 6. The tracking means 440 pinpoints the location of the penetration means 420 with respect to the wall 2 and attachment cuff 22 as viewed on the monitor. The primary and secondary penetration means 420 and 430 are then operated to form treatment specific holes within the cuff 22 and wall 2, as described above. The primary penetration means 420 is then retracted and a fastener is then inserted within the treatment specific hole using the insertion means 450. The location of the penetration apparatus 7 is then adjusted to repeat the process over the area previously viewed by the visualization apparatus 6. The penetration apparatus 7 is then removed and the visualization apparatus 6 is reinserted. The viewing and fastening process is alternately repeated until the attachment cuff 22 is firmly attached to the wall 2.

The repair apparatus 5 is removed once the attachment cuff 22 is secured to the wall 2. The proximal graft assembly 10 is then inserted in an inverted manner through the femoral arteriotomy over the guide wire 160 to the position shown in FIG. 1A. The repair apparatus 5 is then fed through the introducer sheath device 900 over the guide wire 160 from either a femoral or axillary access to a position adjacent the attachment cuff 12. The visualization apparatus 6 and the penetration apparatus 7 are then alternately inserted in the manner described above to secure the attachment cuff 12 to the wall 2. In the event that a standard graft 3 is used, the inverted graft 3 is secured directly to the wall 2 in a similar manner. Alternatively, a self-expanding stent 30 may be used in combination with fasteners to secure the graft 3 to the wall 2. The repair apparatus 5 is then removed.

Once the proximal graft assembly 10 or 3 are secured in place, the first guide wire is removed and the graft 3 or 10 is invaginated. The tubular legs 11 are then inserted into the attachment tubes 22. Self-expanding stents 30 are then used to secure the attachment tubes 22 and tubular legs 11 firmly together. The guide wire 160 is then removed. The positioning assemblies 920 are deflated and the introducer sheath device 900 are removed from the femoral and axillary arteries. The incisions are then closed completing the repair process. The outlined procedure according to the present invention is far less intrusive than current known techniques. As a result, a patient's recovery period should decrease.

Intravascular Ultrasound Repair Method

The intravascular ultrasound repair method will be described in connection with the use of a proximal graft assembly 10 and distal graft assembly 20. Introducer sheath device 900 are placed by femoral arteriotomy in both common iliacs under radiological guidance such that the positioning assembly 920, as described above in connection with the IntraVascular Endoscopy (IVE) based repair method. A distal graft assembly 20 is fed over a guide wire, as described above, until the attachment cuff 21 appears directly above the carina at the bifurcation, as shown in FIG. 1A.

A second guide wire 160 is now fed under guidance between one femoral incision and the left axillary incision. Another introducer sheath device 900 is fed from the axillary until the positioning assembly 920 reaches the infrarenal aorta at which time it is inflated. The repair apparatus 50 is then fed through the introducer sheath device 900 over guide wire 160 to the midpoint of the aortic aneurysm. The visualization apparatus 600 is then positioned adjacent the area of the wall 2 to which the attachment cuff 22 is to be attached. The scanning catheter is drawn caudad providing images of the distal aortal common iliac transition on an external monitor. The repair apparatus 50 is then oriented such that the penetration apparatus 700 is adjacent the area where the attachment cuff 21 is to be attached to the wall 2.

The primary and secondary penetration means 420 and 430 are then operated to form treatment specific holes within the cuff 22 and wall 2, as described above. The primary penetration means 420 is then retracted and a fastener is then inserted within the treatment specific hole using the insertion means 450. The location of the penetration apparatus 700 is then adjusted to repeat the process over the area previously viewed by the visualization apparatus 600. The repair apparatus 50 is then oriented such that the visualization apparatus 600 may scan another portion of the wall 2. The viewing and mounting process is alternately repeated until the attachment cuff 22 is firmly attached to the wall 2.

The repair apparatus 50 is removed once the attachment cuff 22 is secured to the wall 2. The proximal tube graft assembly 10 is then inserted in an inverted manner over the guide wire 160 to the position shown in FIG. 1A. The repair apparatus 50 is then inserted through a femoral incision over the guide wire 160 to a position adjacent the attachment cuff 12. The visualization apparatus 600 and the penetration apparatus 700 are then alternately operated in the manner described above to secure the attachment cuff 12 to the wall 2.

Once the proximal graft assembly 10 is secured in place, the first guide wire and the repair apparatus 50 are removed and the proximal graft assembly 10 is invaginated. The tubular legs 11 are then inserted into the attachment tubes 22 or vice verse. Self-expanding stents 30 are then used to secure the attachment tube 22 and tubular legs 11 firmly together. The guide wire 160 is then removed. The positioning assemblies 920 are deflated and the introducer sheath devices 900 are removed from the femoral and axillary arteries. The incisions are then closed completing the repair process.

While this invention has been described in conjunction with specific embodiments thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined in the following claims.

What is claimed is:

1. A visualization apparatus for viewing an interior of a vessel, wherein the vessel contains blood, said visulization apparatus comprising:
    a housing;
    illumination means for illuminating an area within the vessel for viewing by a user, wherein said illumination means is located within said housing;
    diverting means for temporarily diverting the blood away from the area to be viewed, wherein said diverting means comprises means for supplying fluid to the area to divert the flow of blood away from the area and return means for returning blood to the area, and wherein said diverting means is located within said housing; and
    optical viewing means for viewing the area within the vessel, wherein said optical viewing means is located within said housing.

2. The visualization apparatus according to claim 1, wherein said illumination means comprises optical fiber for illuminating the area within the vessel.

3. The visualization apparatus according to claim 1, wherein said fluid is one of a saline solution and a similar biocompatible.

4. The visualization apparatus according to claim 1, wherein said optical viewing means comprises at least one optical fiber.

5. The visualization apparatus according to claim 1, further comprising scanning means for scanning an area of the vessel for creating an image of the area, wherein said scanning means is located within said housing comprises a scanning catheter.

6. The visualization apparatus according to claim 5, wherein said scanning means produces an ultrasound image.

7. A penetration apparatus for use in forming a treatment specific hole in a vessel that may contain a calcified portion therein for fastening a repair graft to the wall of said vessel, said penetration apparatus comprising:
    a housing;
    penetration means for forming a treatment specific hole in the vessel through the potentially calcified portion, wherein said penetration means is located within said housing; and
    secondary penetration means for forming at least one temporary hole adjacent the treatment specific hole in the vessel through the calcified portion.

8. The penetration apparatus according to claim 7, wherein said penetration means comprises a laser.

9. The penetration apparatus according to claim 8, wherein said laser is an acousto-optical laser.

10. The penetration apparatus according to claim 9, wherein said acousto-optical laser operates at a wavelength about 1.35 $\mu$m.

11. The penetration apparatus according to claim 8, wherein said laser is a Holmium-Yag laser.

12. The penetration apparatus according to claim 11, wherein said Holmium-Yag laser operates at a wavelength about 2.1 $\mu$m.

13. The penetration apparatus according to claim 7, wherein said penetration means comprises a piezoelectric penetrating device.

14. The penetration apparatus according to claim 7, further comprising:
    insertion means for inserting a fastener through the treatment specific hole in the vessel to secure a surgical component to the vessel.

15. The penetration apparatus according to claim 14, wherein said surgical component air graft assembly.

16. The penetration apparatus according to claim 7, wherein said secondary penetration means comprises a laser.

17. The penetration apparatus according to claim 7, wherein said laser is an acousto-optical laser.

18. The penetration apparatus according to claim 17, wherein said acousto-optical laser operates at a wavelength about 1.35 $\mu$m.

19. The penetration apparatus according to claim 16, wherein said laser is a Holmium-Yag laser.

20. The penetration apparatus according to claim 19, wherein said Holmium-Yag laser operates at a wavelength about 2.1 $\mu$m.

21. The penetration apparatus according to claim 7, wherein said penetration means comprises a piezoelectric penetrating device.

22. The penetration apparatus according to claim 7, further comprising:
    insertion means for inserting a fastener through the treatment specific hole in the vessel to secure a surgical component to the vessel.

23. The penetration apparatus according to claim 7, wherein said secondary penetration means stabilizes said penetration apparatus as said insertion means inserts a fastener in the treatment specific hole.

24. The penetration apparatus according to claim 14, further comprising:
    secondary penetration means for forming at least one temporary hole adjacent the treatment specific hole in the vessel through the calcified portion.

25. The penetration apparatus according to claim 7, further comprising:
    tracking means for tracking the location of said penetration apparatus within the vessel.

26. A repair apparatus for repairing a vessel during a surgical procedure, said apparatus comprising:
    a housing; and at least one of a penetration apparatus for use in forming a treatment specific hole in a vessel having a calcified portion and a visualization apparatus for viewing an interior of a vessel during a surgical procedure, wherein said penetration apparatus comprises a penetration housing, and penetration means for forming a treatment specific hole in the potentially calcified vessel wall, and wherein said visualization apparatus comprises a visualization housing, and image creating means for creating an image of the interior of the vessel from within the vessel, wherein said image creating means comprises diverting means for temporarily diverting the blood away from the area for viewing, wherein said diverting means comprises means for supplying a flow of fluid to the area to divert the flow of blood away from the area, and return means for returning blood to the area.

27. The repair apparatus according to claim 26, wherein said housing is capable of interchangeably receiving said penetration apparatus and said visualization apparatus during a surgical procedure.

28. The repair apparatus according to claim 26, wherein said repair apparatus comprises said penetration apparatus and said visualization apparatus for viewing an interior of a vessel during a surgical procedure.

29. The repair apparatus according to claim 28, wherein the vessel contains blood, wherein said image creating means further comprises: illumination means for illuminating an area within the vessel for viewing by a user; and optical viewing means for viewing the area within the vessel.

30. The repair apparatus according to claim 29, wherein said illumination means comprises an optical fiber for illuminating the area within the vessel.

31. The repair apparatus according to claim 29, wherein said diverting means comprises:

means for supplying a flow of fluid to the area to divert the flow of blood away from the area; and return means for returning blood to the area.

32. The repair apparatus according to claim 26, wherein said fluid is a saline solution.

33. The repair apparatus according to claim 29, wherein said optical viewing means comprises an optical fiber.

34. The repair apparatus according to claim 29, wherein said visualization means comprises scanning means for scanning an area of the vessel for creating an image of the area.

35. The repair apparatus according to claim 34, wherein said scanning means produces an ultrasound image.

36. The repair apparatus according to claim 34, wherein said scanning means comprises a scanning catheter.

37. The repair apparatus according to claim 29, wherein said penetration means comprises a laser.

38. The repair apparatus according to claim 37, wherein said laser is an acousto-optical laser.

39. The repair apparatus according to claim 38, wherein said laser operates at a wavelength about 1.35 $\mu$m.

40. The repair apparatus according to claim 37, wherein said laser is a Holmium-Yag laser.

41. The repair apparatus according to claim 40, wherein said laser operates at a wavelength about 2.1 $\mu$m.

42. The repair apparatus according to claim 29, wherein said penetration means comprises a piezoelectric penetrating device.

43. The repair apparatus according to claim 29, further comprising:

insertion means for inserting a fastener through the treatment specific hole in the vessel to secure a surgical component to the vessel.

44. The repair apparatus according to claim 43, wherein said surgical component is a repair graft assembly.

45. The repair apparatus according to claim 44, further comprising:

secondary penetration means for forming at least one temporary hole adjacent the treatment specific hole in the potentially calcified vessel wall.

46. The repair apparatus according to claim 45, wherein said secondary penetration means comprises a laser.

47. The repair apparatus according to claim 46, wherein said laser is an acousto-optical laser.

48. The penetration apparatus according to claim 47, wherein said acousto-optical laser operates at a wavelength about 1.35 $\mu$m.

49. The repair apparatus according to claim 46, wherein said laser is a Holmium-Yag laser.

50. The penetration apparatus according to claim 49, wherein said Holmium-Yag laser operates at a wavelength about 2.1 $\mu$m.

51. The repair apparatus according to claim 45, wherein said secondary penetration means comprises a piezoelectric penetrating device.

52. The repair apparatus according to claim 45, wherein said secondary penetration means stabilizes said penetration apparatus as said insertion means inserts a fastener in the treatment specific hole.

53. A penetration apparatus for use in forming a treatment specific hole in a vessel that may contain a calcified portion therein for fastening a repair graft to the wall of said vessel, said penetration apparatus comprising:

a housing;

penetration means for forming a treatment specific hole in the vessel through the potentially calcified portion, wherein said penetration means is located within said housing; and insertion means for inserting a fastener through the treatment specific hole in the vessel to secure a surgical component to the vessel.

54. The penetration apparatus according to claim 53 further comprising:

secondary penetration means for forming at least one temporary hole adjacent the treatment specific hole in the vessel through the calcified portion.

55. A repair apparatus for repairing a vessel during a surgical procedure, said apparatus comprising:

a housing; and at least one of a penetration apparatus for use in forming a treatment specific hole in a vessel having a calcified portion and a visualization apparatus for viewing an interior of a vessel during a surgical procedure, wherein said penetration apparatus comprises a penetration housing, and penetration means for forming a treatment specific hole in the potentially calcified vessel wall, and wherein said visualization apparatus comprises a visualization housing, and image creating means for creating an image of the interior of the vessel from within the vessel, and insertion means for inserting a fastener through the treatment specific hole in the vessel to secure a surgical component to the vessel.

* * * * *